(12) United States Patent
Boyd et al.

(10) Patent No.: US 7,208,526 B2
(45) Date of Patent: Apr. 24, 2007

(54) STYRYLSULFONAMIDES

(75) Inventors: Edward Boyd, Reading (GB);
Frederick Brookfield, Benson (GB);
Jonathan Gridley, Reading (GB);
Matthias Koerner, Antdorf (DE);
Manfred Kubbies, Penzberg (DE);
Raymond Lau, Bracknell (GB); Ulrike Reiff, Penzberg (DE); Georg Tiefenthaler, Sindelsdorf (DE);
Wolfgang von der Saal, Murnau (DE);
Timothy Woodcock, Munich (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/414,042

(22) Filed: Apr. 28, 2006

(65) Prior Publication Data
US 2006/0270874 A1    Nov. 30, 2006

(30) Foreign Application Priority Data
May 20, 2005   (EP) .................................. 05010982
Jan. 18, 2006   (EP) .................................. 06001007

(51) Int. Cl.
*A61K 31/18*   (2006.01)
*C07C 311/51*   (2006.01)

(52) U.S. Cl. .................... 514/604; 514/602; 514/603; 564/84; 564/85; 564/86; 564/87; 564/88; 564/89; 564/90; 564/92

(58) Field of Classification Search ............... 514/602, 514/603, 604; 564/84, 85, 86, 87, 88, 89, 564/90, 92
See application file for complete search history.

(56) References Cited

U.S. PATENT DOCUMENTS

| 3,983,107 | A | | 9/1976 | Holland |
| 4,157,257 | A | | 6/1979 | Takematsu et al. |
| 4,206,142 | A | | 6/1980 | Matier et al. |
| 6,166,064 | A | * | 12/2000 | Dombroski et al. ........ 514/452 |
| 6,251,827 | B1 | * | 6/2001 | Ziemer et al. .............. 504/130 |
| 6,348,474 | B1 | | 2/2002 | Kayakiri et al. |
| 6,410,584 | B1 | | 6/2002 | Pamukcu et al. |
| 6,911,469 | B2 | | 6/2005 | Kayakiri et al. |
| 2002/0099212 | A1 | | 7/2002 | Kayakiri et al. |

2004/0180947 A1    9/2004   Kayakiri et al.

FOREIGN PATENT DOCUMENTS

| WO | WO 94/27979 | 12/1994 |
| WO | WO 99/00372 | 1/1999 |
| WO | WO 02/098848 | 12/2002 |
| WO | WO 2004/048329 | 6/2004 |

OTHER PUBLICATIONS

Hirooka et al., Bull. Chem. Soc. Jap., 64, pp. 1431-1433 (1991).
Harada et al., Bioorg. Med. Chem. 9, pp. 2955-2968 (2001).
Thompson, M.E., J. Org. Chem., 49, pp. 1700-1703 (1984).
Aramini et al., J. Org. Chem., 68, pp. 7911-7914 (2003).
Harada et al., Chem. Pharm. Bull., 49, pp. 1593-1603 (2001).
Kameyama et al., Bull. Chem. Soc. Jap., 61 pp. 1231-1235 (1988).
Beers et al., Bioorg. Med. Chem., 5, pp. 779-786 (1997).
Horne et al., J. Chem. Soc. Chem. Commun., 15, pp. 1046-1048 (1991).
Borthwick et al., J. Med. Chem., 43, pp. 4452-4464 (2000).
Boger et al., J. Org. Chem., 55, pp. 1379-1390 (1990).
Matier et al., J. Med. Chem., 17, pp. 549-552 (1974).
Reddy et al., Org. Prep. Proced. Int., 23, pp. 633-638 (1991).
Reddy et al., Phosphorus, Sulfur Silicon Relat. Elem., 53, pp. 285-290 (1990).
Wipf et al., Bioorg. Med. Chem. Lett., 11, pp. 313-317 (2001).
Bastin et al., Organic Proc. Res. Dev., 4, pp. 427-435 (2000).

* cited by examiner

*Primary Examiner*—Peter O'Sullivan
(74) *Attorney, Agent, or Firm*—George W. Johnston; Patricia S. Rocha-Tramaloni; Brian C. Remy

(57) ABSTRACT

The present invention relates to the compounds of formula I:

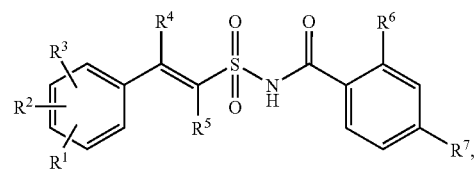

formula I their pharmaceutically acceptable salts or esters, enantiomeric forms, diastereoisomers and racemates, the preparation of the above compounds, pharmaceutical compositions containing them and their manufacture, as well as the use of such compounds in the control or prevention of illnesses such as cancer.

55 Claims, No Drawings

STYRYLSULFONAMIDES

PRIORITY TO RELATED APPLICATIONS

This application claims the benefit of European Application No. 05010982.6, filed May 20, 2005 and European Application No. 06001007.1, filed Jan. 18, 2006, which are hereby incorporated by reference in their entirety.

FIELD OF THE INVENTION

The present invention relates to novel styrylsulfonamide derivatives, to a process for their manufacture, pharmaceutical compositions containing them and their manufacture as well as the use of these compounds as pharmaceutically active agents.

BACKGROUND OF THE INVENTION

The treatment of cancer diseases is of great importance in medicine. There is a worldwide need for effective cancer therapies in order to achieve a treatment which is appropriate to a patient and is target-orientated. This can be seen in the large number of scientific studies which have recently appeared in the fields of applied oncology and fundamental research relating to cancer therapy. The effects of tumor inhibitors are due to a very wide variety of mechanisms, only some of which are known. It is not unusual for known tumor drugs to be found to have new mechanisms of action. This is also to be expected in the case of the compounds according to the invention. Many tumor drugs act by way of mechanisms such as blockading the mechanism of cell division in the cell, preventing the tumor from being supplied with nutrients and oxygen (antiangiogenesis), preventing metastasis, preventing the reception and the onward transmission of growth signals to the tumor cell or forcing the tumor cell into programmed cell death (apoptosis).

Because they have different mechanisms of action, including interacting with different intracellular targets, the clinically relevant cytostatic agents are frequently administered in combination in order to achieve a synergistic therapeutic effect.

Some styrylsulfonamide derivatives are known as inhibitors of neoplastic cells from U.S. Pat. No. 6,410,584 B1. WO 99/00372 relates to styrylsulfonamide derivatives as hypoglycemics. U.S. Pat. No. 4,206,142 describes styrylsulfonamides as intermediates of analgetic styrylsulfonylamidines and Hirooka, S., et al, Bull. Chem. Soc. Jap. 64 (1991) 1431–1433 relates to the synthesis of styrylsulfonamide derivatives.

WO 02/098848 and WO 2004/048329 relate to benzoylsulfonamides as antitumor agents.

SUMMARY OF THE INVENTION

The present invention relates to styrylsulfonamides of the general formula I and all pharmaceutically acceptable salts or esters thereof wherein formula I is:

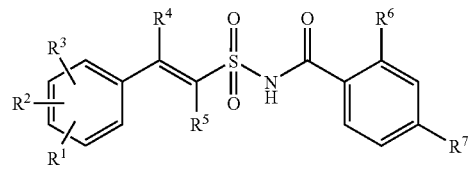

formula I wherein:
(a) $R^1$, $R^2$ and $R^3$ are independently selected from the group consisting of hydrogen, halogen, alkyl, alkoxy, alkylsulfanyl, halogenated alkyl, halogenated alkoxy, halogenated alkylsulfanyl, nitro, amino, alkylamino, dialkylamino, cyano, hydroxyl, and heterocyclyl;
(b) $R^4$ and $R^5$ are independently selected from the group consisting of hydrogen and alkyl;
(c) $R^6$ is selected from the group consisting of chlorine, bromine, methyl, trifluoromethyl and methoxy; and
(d) $R^7$ is selected from the group consisting of chlorine, bromine, fluorine, methyl and trifluoromethyl.

The compounds according to this invention show antiproliferative activity and inhibit the growth of tumor cells in vitro and in vivo. The present invention provides the compounds of formula I and their tautomers, pharmaceutically acceptable salts or esters, enantiomeric forms, diastereoisomers and racemates, their use for the inhibition of tumor growth, the preparation of the above-mentioned compounds, compositions containing them and their manufacture as well as the use of the above-mentioned compounds in the control or prevention of illnesses, especially cancers such as colorectal cancer, breast cancer, lung, prostate, pancreatic, gastric, bladder, ovarian, melanoma, neuroblastoma, cervical, kidney or renal cancers, leukemias or lymphomas, or in the manufacture of corresponding pharmaceutical compositions.

DETAILED DESCRIPTION OF THE INVENTION

The term "alkyl" as used herein means a saturated, straight-chain or branched-chain hydrocarbon containing from 1 to 6 carbon atoms, preferably 1 to 4 carbon atoms, such as methyl, ethyl, n-propyl, isopropyl, n-butyl, 2-butyl, t-butyl, n-pentyl, 3-methyl-butyl, 2-methyl-butyl, n-hexyl, 3-methyl-pentyl, 2-ethyl-butyl, 3,3-dimethyl-butyl, 2,2-dimethyl-butyl or 2,3-dimethyl-butyl.

In a particular embodiment of the invention, the alkyl as used in $R^4$ and $R^5$ denotes a $(C_{1-C3})$alkyl group, preferably an ethyl or methyl group and more preferably a methyl group.

The term "alkoxy" as used herein means an alkyl-O— group wherein the alkyl is defined as above.

The term "alkylsulfanyl" as used herein means an alkyl-S— group wherein the alkyl is defined as above.

The term "alkylamino" as used herein means an alkyl-NH— group wherein the alkyl is defined as above.

The term "dialkylamino" as used herein means an $(alkyl)_2$N— group wherein the alkyl is defined as above.

The term "halogenated alkyl" as used herein means an alkyl group as defined above which is substituted one or more times by halogen, preferably by fluorine or chlorine, especially by fluorine. Examples are difluoromethyl, trifluoromethyl, 2,2,2-trifluoroethyl, perfluorethyl, and the like, especially trifluoromethyl.

The term "halogenated alkoxy" as used herein means an alkoxy group as defined above which is substituted one or more times by halogen, preferably by fluorine or chlorine, especially by fluorine. Examples are difluoromethoxy, trifluoromethoxy, 2,2,2-trifluoroethoxy, perfluoroethoxy and the like, especially trifluoromethoxy.

The term "halogenated alkylsulfanyl" as used herein means an alkylsulfanyl group as defined above which is substituted one or more times by halogen, preferably by fluorine or chlorine, especially by fluorine. Examples are trifluoromethylsulfanyl, difluoromethylsulfanyl, perfluoroethylsulfanyl and the like, especially trifluoromethylsulfanyl.

The term "halogen" as used in the definitions of means fluorine, chlorine, bromine or iodine, preferably fluorine, chlorine or bromine and especially fluorine or chlorine.

The term "heterocyclyl" means a saturated, monocyclic ring with 5 to 6 ring atoms which contains up to 3 heteroatoms, preferably 1 or 2 heteroatoms, independently selected from the group consisting of N, O and S with the remaining ring atoms being carbon atoms. Such saturated heterocyclic groups can be optionally substituted one to three times, preferably one or two times, by alkyl as defined above, preferably by methyl. Examples of such saturated heterocyclic groups are pyrrolidinyl, morpholinyl, piperazinyl, N-methyl-piperazinyl, piperidyl and the like, preferably morpholinyl.

As used herein, in relation to mass spectrometry (MS) the term "API+" refers to positive atmospheric pressure ionization mode, the term "API–" refers to negative atmospheric pressure ionization mode, the term "ESI+" refers to positive electrospray ionization mode, and the term "M+H" refers to protonated molecular ions.

In relation to the processes described herein for the preparation of the compounds of the present invention, the term "activated before" means that the carboxylic acid group is converted into a reactive carboxylic acid derivative before the reaction. Such activation is typically carried out without solvent, or in solvents like dichloromethane, dichloroethane, tetrahydrofuran, dioxane and mixtures thereof, at temperatures between 0° C. and 100° C. Typical methods used for the activation are chlorination or formation of an imidazolide. Typically used chlorinating reagents are thionylchloride, oxalyl chloride, phosphorus trichloride, phosphorus pentachloride, phosphorus oxychloride, N-chlorosuccinamide triphenylphosphine. A typically used imidazolination method is the reaction with N,N'-carbonyl diimidazole (CDI). Other typically used activation methods include the use of activating agents such as 1-ethyl-3-(3'-dimethylaminopropyl)carbodiimide (EDCI), hydroxy-benzotriazole (HOBt) and the like.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts or esters. The term "pharmaceutically acceptable salt" refers to conventional acid-addition salts that retain the biological effectiveness and properties of the compounds of formula I and are formed from suitable non-toxic organic or inorganic bases or, if $R^1$ to $R^3$ is e.g. amino or alkylamino, from organic or inorganic acids or. Examples of base-addition salts include those derived from sodium, potassium, ammonium, quaternary ammonium hydroxides (such as for example, tetramethylammonium hydroxide), especially from sodium. Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Stahl, P. H., and Wermuth, G., (editors), Handbook of Pharmaceutical Salts, Verlag Helvetica Chimica Acta (VHCA), Zütrich, (2002) or Bastin, R. J., et al., Organic Proc. Res. Dev. 4 (2000) 427–435.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively, separation of the enantiomers can also be achieved by using chromatography on chiral HPLC-phases which are commercially available.

$R^1$, $R^2$ and $R^3$ of formula I are independently selected from the group consisting of hydrogen, halogen, alkyl, alkoxy, alkylsulfanyl, halogenated alkyl, halogenated alkoxy, halogenated alkylsulfanyl, nitro, amino, alkylamino, dialkylamino, cyano, hydroxyl, and heterocyclyl. Preferably one or two of $R^1$, $R^2$ and $R^3$ represents hydrogen. In one embodiment of the invention $R^3$ represents hydrogen, in another embodiment $R^2$ and $R^3$ represent hydrogen. The position of $R^1$ on the phenyl residue is preferably ortho to the ethenyl substituent.

$R^4$ and $R^5$ independently represent hydrogen or alkyl, preferably hydrogen.

$R^6$ is chlorine, bromine, methyl, trifluoromethyl or methoxy, preferably chlorine, bromine, trifluoromethyl or methoxy, and more preferably chlorine.

$R^7$ is chlorine, fluorine, methyl or trifluoromethyl, preferably chlorine, bromine, fluorine or trifluoromethyl, and more preferably chlorine.

One embodiment of the invention are the compounds of formula I, wherein $R^6$ and $R^7$ are both chlorine.

Another embodiment of the invention are the compounds of formula I, wherein $R^4$ and $R^5$ are both hydrogen.

Another embodiment of the invention are the compounds of formula I, wherein $R^1$, $R^2$ and $R^3$ are independently selected from the group consisting of hydrogen, halogen, alkyl, alkoxy, halogenated alkyl, halogenated alkoxy, dialkylamino, hydroxyl, and heterocyclyl.

Another embodiment of the invention are the compounds of formula I, wherein:
  (a) $R^1$, $R^2$ and $R^3$ are independently selected from the group consisting of hydrogen, halogen, alkyl, alkoxy, halogenated alkyl, halogenated alkoxy, dialkylamino, hydroxyl, and heterocyclyl; and
  (b) $R^4$ and $R^5$ are both hydrogen.

Another embodiment of the invention are the compounds of formula I, wherein $R^1$, $R^2$ and $R^3$ are independently selected from the group consisting of hydrogen, halogen, alkyl, alkoxy, halogenated alkyl, halogenated alkoxy, dialkylamino, and hydroxy.

Another embodiment of the invention are the compounds of formula I, wherein:
  (a) $R^1$, $R^2$ and $R^3$ are independently selected from the group consisting of hydrogen, halogen, alkyl, alkoxy, halogenated alkyl, halogenated alkoxy, dialkylamino and hydroxy; and
  (b) $R^4$ and $R^5$ are both hydrogen.

Another embodiment of the invention are the compounds of formula I, wherein $R^1$, $R^2$ and $R^3$ are independently selected from the group consisting of hydrogen, halogen, alkyl, alkoxy, halogenated alkyl, halogenated alkoxy, and heterocyclyl.

Another embodiment of the invention are the compounds of formula I, wherein:
  (a) $R^1$, $R^2$ and $R^3$ are independently selected from the group consisting of hydrogen, halogen, alkyl, alkoxy, halogenated alkyl, halogenated alkoxy and heterocyclyl; and
  (b) $R^4$ and $R^5$ are both hydrogen.

Another embodiment of the invention are the compounds of formula I, wherein $R^3$ is hydrogen.

Another embodiment of the invention are the compounds of formula I, wherein:
  (a) $R^1$ and $R^2$ are independently selected from the group consisting of hydrogen, halogen, alkyl, alkoxy, halogenated alkyl, halogenated alkoxy and heterocyclyl; and
  (b) $R^3$ is hydrogen.

Another embodiment of the invention are the compounds of formula I, wherein:
  (a) $R^1$ and $R^2$ are independently selected from the group consisting of hydrogen, halogen, alkyl, alkoxy, halogenated alkyl, halogenated alkoxy, and heterocyclyl;
  (b) $R^4$ and $R^5$ are both hydrogen; and
  (c) $R^3$ is hydrogen.

Another embodiment of the invention are the compounds of formula I, wherein:
  (a) $R^1$ and $R^2$ are both halogen;
  (b) $R^4$ and $R^5$ are both hydrogen; and
  (c) $R^3$ is hydrogen.

Another embodiment of the invention are the compounds of formula I, wherein:
  (a) $R^1$ and $R^2$ are both halogen;
  (b) $R^4$ and $R^5$ are both hydrogen;
  (c) $R^3$ is hydrogen; and
  (d) $R^6$ and $R^7$ are both chlorine.

Another embodiment of the invention are the compounds of formula I, wherein:
  (a) $R^1$, $R^2$ and $R^3$ independently represent halogen;
  (b) $R^4$ and $R^5$ are both hydrogen;
  (c) $R^6$ and $R^7$ are both chlorine.

Such compounds may, for example, be selected from the group consisting of:
  (a) (E)-2-(4-Chloro-phenyl)-ethenesulfonic acid 2,4-dichloro-benzoylamide;
  (b) (E)-2-(3-Chloro-phenyl)-ethenesulfonic acid 2,4-dichloro-benzoylamide;
  (c) (E)-2-(2-Chloro-phenyl)-ethenesulfonic acid 2,4-dichloro-benzoylamide;
  (d) (E)-2-(2,4-Difluoro-phenyl)-ethenesulfonic acid 2,4-dichloro-benzoylamide;
  (e) (E)-2-(3,4-Dichloro-phenyl)-ethenesulfonic acid 2,4-dichloro-benzoylamide;
  (f) (E)-2-(2-Fluoro-phenyl)-ethenesulfonic acid 2,4-dichloro-benzoylamide; and
  (g) (E)-2-(2,4,6-Trifluoro-phenyl)-ethenesulfonic acid 2,4-dichloro-benzoylamide; sodium salt.

Another embodiment of the invention are the compounds of formula I, wherein:
  (a) $R^1$ and $R^2$ are independently selected from the group consisting of halogenated alkyl and halogenated alkoxy;
  (b) $R^4$ and $R^5$ are both hydrogen; and
  (c) $R^3$ is hydrogen.

Another embodiment of the invention are the compounds of formula I, wherein:
  (a) $R^1$ and $R^2$ are independently selected from the group consisting of halogenated alkyl and halogenated alkoxy;
  (b) $R^4$ and $R^5$ are both hydrogen;
  (c) $R^3$ is hydrogen; and
  (d) $R^6$ and $R^7$ are both chlorine.

Such compounds may, for example, be selected from the group consisting of:
  (a) (E)-2-(4-Trifluoromethyl-phenyl)-ethenesulfonic acid 2,4-dichloro-benzoylamide; and
  (b) (E)-2-(4-Trifluoromethoxy-phenyl)-ethenesulfonic acid 2,4-dichloro-benzoylamide.

Another embodiment of the invention are the compounds of formula I, wherein:
  (a) $R^1$ and $R^2$ are independently selected from the group consisting of hydrogen, alkyl, alkoxy, dialkylamino and hydroxy;
  (b) $R^4$ and $R^5$ are both hydrogen; and
  (c) $R^3$ is hydrogen.

Another embodiment of the invention are the compounds of formula I, wherein
  (a) $R^1$ and $R^2$ are independently selected from the group consisting of hydrogen, alkyl, alkoxy, dialkylamino, and hydroxy;
  (b) $R^4$ and $R^5$ are both hydrogen;
  (c) $R^3$ is hydrogen; and
  (d) $R^6$ and $R^7$ are both chlorine.

Such compounds may, for example, be selected from the group consisting of:
  (a) (E)-2-Phenyl-ethenesulfonic acid 2,4-dichloro-benzoylamide;

(b) (E)-2-(2,4-Dimethyl-phenyl)-ethenesulfonic acid 2,4-dichloro-benzoylamide;
(c) (E)-2-(2-Methoxy-phenyl)-ethenesulfonic acid 2,4-dichloro-benzoylamide;
(d) (E)-2-(2-Dimethylamino-phenyl)-ethenesulfonic acid 2,4-dichloro-benzoylamide;
(e) (E)-2-o-Tolyl-ethenesulfonic acid 2,4-dichloro-benzoylamide;
(f) (E)-2-(3-Hydroxy-phenyl)-ethenesulfonic acid 2,4-dichloro-benzoylamide;
(g) (E)-2-(4-Hydroxy-phenyl)-ethenesulfonic acid 2,4-dichloro-benzoylamide; and
(h) (E)-2-(2-Hydroxy-phenyl)-ethenesulfonic acid 2,4-dichloro-benzoylamide.

Another embodiment of the invention are the compounds of formula I, wherein $R^4$ is alkyl.

Another embodiment of the invention are the compounds of formula I, wherein $R^4$ is alkyl and $R^5$ is hydrogen.

Another embodiment of the invention are the compounds of formula I, wherein:
(a) $R^1$ and $R^2$ are independently selected from the group consisting of hydrogen, halogen, alkyl, alkoxy, halogenated alkyl, halogenated alkoxy, and heterocyclyl;
(b) $R^4$ is alkyl;
(c) $R^5$ is hydrogen; and
(d) $R^3$ is hydrogen.

Another embodiment of the invention are the compounds of formula I, wherein:
(a) $R^1$ and $R^2$ are independently selected from the group consisting of hydrogen, halogen, alkyl, alkoxy, halogenated alkyl, halogenated alkoxy, and heterocyclyl;
(b) $R^4$ is alkyl;
(c) $R^5$ is hydrogen;
(d) $R^3$ is hydrogen; and
(e) $R^6$ and $R^7$ are both chlorine.

Such a compound may, for example, be:
(E)-2-Phenyl-propene-1-sulfonic acid 2,4-dichloro-benzoylamide.

Another embodiment of the invention are the compounds of formula I, wherein $R^5$ is alkyl.

Another embodiment of the invention are the compounds of formula I, wherein:
(a) $R^4$ is hydrogen; and
(b) $R^5$ is alkyl.

Another embodiment of the invention are the compounds of formula I, wherein:
(a) $R^1$ and $R^2$ are independently selected from the group consisting of hydrogen, halogen, alkyl, alkoxy, halogenated alkyl, halogenated alkoxy, and heterocyclyl;
(b) $R^4$ is hydrogen;
(c) $R^5$ is alkyl; and
(d) $R^3$ is hydrogen.

Another embodiment of the invention are the compounds of formula I, wherein:
(a) $R^1$ and $R^2$ are independently selected from the group consisting of hydrogen, halogen, alkyl, alkoxy, halogenated alkyl, halogenated alkoxy, and heterocyclyl;
(b) $R^4$ is hydrogen;
(c) $R^5$ is alkyl;
(d) $R^3$ is hydrogen; and
(e) $R^6$ and $R^7$ are both chlorine.

Such a compound may, for example, be:
(E)-1-Phenyl-propene-2-sulfonic acid 2,4-dichloro-benzoylamide.

Another embodiment of the invention are the compounds of formula I, wherein $R^4$ and $R^5$ are both alkyl.

Another embodiment of the invention are the compounds of formula I, wherein $R^6$ is chlorine and $R^7$ is bromine.

Such compounds may, for example, be selected from the group consisting of:
(a) (E)-2-(2,4-Dimethyl-phenyl)-ethenesulfonic acid 4-bromo-2-chloro-benzoylamide; sodium salt;
(b) (E)-2-(3-Methoxy-phenyl)-ethenesulfonic acid 4-bromo-2-chloro-benzoylamide; sodium salt;
(c) (E)-2-(2-Methoxy-phenyl)-ethenesulfonic acid 4-bromo-2-chloro-benzoylamide; sodium salt;
(d) (E)-2-(3-Chloro-phenyl)-ethenesulfonic acid 4-bromo-2-chloro-benzoylamide; sodium salt;
(e) (E)-2-(2-Chloro-phenyl)-ethenesulfonic acid 4-bromo-2-chloro-benzoylamide; sodium salt;
(f) (E)-2-(3,4-Dichloro-phenyl)-ethenesulfonic acid 4-bromo-2-chloro-benzoylamide; sodium salt;
(g) (E)-2-Phenyl-ethenesulfonic acid 4-bromo-2-chloro-benzoylamide; sodium salt;
(h) (E)-2-(4-Trifluoromethyl-phenyl)-ethenesulfonic acid 4-bromo-2-chloro-benzoylamide; sodium salt; and
(i) (E)-2-(4-Trifluoromethoxy-phenyl)-ethenesulfonic acid 4-bromo-2-chloro-benzoylamide; sodium salt.

Another embodiment of the invention are the compounds of formula I, wherein $R^6$ is chlorine; and $R^7$ is fluorine.

Such compounds may, for example, be selected from the group consisting of:
(a) (E)-2-(3-Methoxy-phenyl)-ethenesulfonic acid 2-chloro-4-fluoro-benzoylamide; sodium salt;
(b) (E)-2-(2-Methoxy-phenyl)-ethenesulfonic acid 2-chloro-4-fluoro-benzoylamide; sodium salt;
(c) (E)-2-(3-Chloro-phenyl)-ethenesulfonic acid 2-chloro-4-fluoro-benzoylamide; sodium salt;
(d) (E)-2-(2,4-Difluoro-phenyl)-ethenesulfonic acid 2-chloro-4-fluoro-benzoylamide; sodium salt;
(e) (E)-2-(4-Chloro-phenyl)-ethenesulfonic acid 2-chloro-4-fluoro-benzoylamide; sodium salt;
(f) (E)-2-(4-Methoxy-phenyl)-ethenesulfonic acid 2-chloro-4-fluoro-benzoylamide; sodium salt;
(g) (E)-2-(4-Trifluoromethyl-phenyl)-ethenesulfonic acid 2-chloro-4-fluoro-benzoylamide; sodium salt;
(h) (E)-2-(2,4-Dimethyl-phenyl)-ethenesulfonic acid 2-chloro-4-fluoro-benzoylamide; sodium salt;
(i) (E)-2-(4-Trifluoromethoxy-phenyl)-ethenesulfonic acid 2-chloro-4-fluoro-benzoylamide; sodium salt;
(j) (E)-2-Phenyl-ethenesulfonic acid 2-chloro-4-fluoro-benzoylamide; sodium salt;
(k) (E)-2-(3,4-Dichloro-phenyl)-ethenesulfonic acid 2-chloro-4-fluoro-benzoylamide; sodium salt; and
(l) (E)-2-(3,5-Dichloro-phenyl)-ethenesulfonic acid 2-chloro-4-fluoro-benzoylamide; sodium salt.

Another embodiment of the invention are the compounds of formula I, wherein $R^6$ is bromine and $R^7$ is chlorine.

Such a compound may, for example, be:
(E)-2-Phenyl-ethenesulfonic acid 2-bromo-4-chloro-benzoylamide.

Another embodiment of the invention are the compounds of formula I, wherein $R^6$ is bromine and $R^7$ is fluorine.

Such compounds may, for example, be selected from the group consisting of:
(a) (E)-2-(4-Trifluoromethyl-phenyl)-ethenesulfonic acid 2-bromo-4-fluoro-benzoylamide; sodium salt;
(b) (E)-2-(3-Methoxy-phenyl)-ethenesulfonic acid 2-bromo-4-fluoro-benzoylamide; sodium salt;
(c) (E)-2-(2-Methoxy-phenyl)-ethenesulfonic acid 2-bromo-4-fluoro-benzoylamide; sodium salt;
(d) (E)-2-(3-Chloro-phenyl)-ethenesulfonic acid 2-bromo-4-fluoro-benzoylamide; sodium salt;

(e) (E)-2-(2-Chloro-phenyl)-ethenesulfonic acid 2-bromo-4-fluoro-benzoylamide; sodium salt;
(f) (E)-2-Phenyl-ethenesulfonic acid 2-bromo-4-fluoro-benzoylamide; sodium salt;
(g) (E)-2-(4-Trifluoromethoxy-phenyl)-ethenesulfonic acid 2-bromo-4-fluoro-benzoylamide; sodium salt; and
(h) (E)-2-(3,4-Dichloro-phenyl)-ethenesulfonic acid 2-bromo-4-fluoro-benzoylamide; sodium salt.

Another embodiment of the invention are the compounds of formula I, wherein $R^6$ is bromine and $R^7$ is methyl.

Such compounds may, for example, be selected from the group consisting of:
(a) (E)-2-(3-Methoxy-phenyl)-ethenesulfonic acid 2-bromo-4-methyl-benzoylamide; sodium salt;
(b) (E)-2-(2-Methoxy-phenyl)-ethenesulfonic acid 2-bromo-4-methyl-benzoylamide; sodium salt;
(c) (E)-2-(3-Chloro-phenyl)-ethenesulfonic acid 2-bromo-4-methyl-benzoylamide; sodium salt;
(d) (E)-2-(2-Chloro-phenyl)-ethenesulfonic acid 2-bromo-4-methyl-benzoylamide; sodium salt;
(e) (E)-2-Phenyl-ethenesulfonic acid 2-bromo-4-methyl-benzoylamide; sodium salt;
(f) (E)-2-(3,4-Dichloro-phenyl)-ethenesulfonic acid 2-bromo-4-methyl-benzoylamide; sodium salt; and
(g) (E)-2-(4-Trifluoromethoxy-phenyl)-ethenesulfonic acid 2-bromo-4-methyl-benzoylamide; sodium salt.

Another embodiment of the invention are the compounds of formula I, wherein $R^6$ is methyl and $R^7$ is chlorine.

Such compounds may, for example, be selected from the group consisting of:
(a) (E)-2-(3-Chloro-phenyl)-ethenesulfonic acid 4-chloro-2-methyl-benzoylamide; sodium salt;
(b) (E)-2-(2-Chloro-phenyl)-ethenesulfonic acid 4-chloro-2-methyl-benzoylamide; sodium salt;
(c) (E)-2-Phenyl-ethenesulfonic acid 4-chloro-2-methyl-benzoylamide; sodium salt;
(d) (E)-2-(3-Methoxy-phenyl)-ethenesulfonic acid 4-chloro-2-methyl-benzoylamide; sodium salt; and
(e) (E)-2-(2-Methoxy-phenyl)-ethenesulfonic acid 4-chloro-2-methyl-benzoylamide; sodium salt.

Another embodiment of the invention are the compounds of formula I, wherein $R^6$ is methyl and $R^7$ is bromine.

Such compounds may, for example, be selected from the group consisting of:
(a) 2-(3-Methoxy-phenyl)-ethenesulfonic acid 4-bromo-2-methyl-benzoylamide; sodium salt;
(b) (E)-2-(2-Methoxy-phenyl)-ethenesulfonic acid 4-bromo-2-methyl-benzoylamide; sodium salt;
(c) (E)-2-(3-Chloro-phenyl)-ethenesulfonic acid 4-bromo-2-methyl-benzoylamide; sodium salt;
(d) 2-(2-Chloro-phenyl)-ethenesulfonic acid 4-bromo-2-methyl-benzoylamide; sodium salt;
(e) (E)-2-(3,4-Dichloro-phenyl)-ethenesulfonic acid 4-bromo-2-methyl-benzoylamide; sodium salt;
(f) (E)-2-Phenyl-ethenesulfonic acid 4-bromo-2-methyl-benzoylamide; sodium salt;
(g) (E)-2-(4-Trifluoromethyl-phenyl)-ethenesulfonic acid 4-bromo-2-methyl-benzoylamide; sodium salt; and
(h) (E)-2-(4-Trifluoromethoxy-phenyl)-ethenesulfonic acid 4-bromo-2-methyl-benzoylamide; sodium salt.

Another embodiment of the invention are the compounds of formula I, wherein $R^6$ is methyl and $R^7$ is fluorine.

Another embodiment of the invention are the compounds of formula I, wherein $R^6$ is methyl; and $R^7$ is methyl.

Such compounds may, for example, be selected from the group consisting of:
(a) (E)-2-(3-Methoxy-phenyl)-ethenesulfonic acid 2,4-dimethyl-benzoylamide; sodium salt;
(b) (E)-2-(2-Methoxy-phenyl)-ethenesulfonic acid 2,4-dimethyl-benzoylamide; sodium salt;
(c) (E)-2-(3-Chloro-phenyl)-ethenesulfonic acid 2,4-dimethyl-benzoylamide; sodium salt;
(d) (E)-2-(2-Chloro-phenyl)-ethenesulfonic acid 2,4-dimethyl-benzoylamide; sodium salt;
(e) (E)-2-(3,4-Dichloro-phenyl)-ethenesulfonic acid 2,4-dimethyl-benzoylamide; sodium salt;
(f) (E)-2-(4-Trifluoromethyl-phenyl)-ethenesulfonic acid 2,4-dimethyl-benzoylamide; sodium salt;
(g) (E)-2-(2,4-Dimethyl-phenyl)-ethenesulfonic acid 2,4-dimethyl-benzoylamide; sodium salt; and
(h) (E)-2-(4-Trifluoromethoxy-phenyl)-ethenesulfonic acid 2,4-dimethyl-benzoylamide; sodium salt.

Another embodiment of the invention are the compounds of formula I, wherein $R^6$ is trifluoromethyl and $R^7$ is chlorine.

Such a compound may, for example, be:
(E)-2-Phenyl-ethenesulfonic acid 4-chloro-2-trifluoromethyl-benzoylamide.

Another embodiment of the invention are the compounds of formula I, wherein $R^6$ is trifluoromethyl and $R^7$ is fluorine.

Such compounds may, for example, be selected from the group consisting of:
(a) (E)-2-(2,4-Dimethyl-phenyl)-ethenesulfonic acid 4-fluoro-2-trifluoromethyl-benzoylamide; sodium salt;
(b) (E)-2-(3-Methoxy-phenyl)-ethenesulfonic acid 4-fluoro-2-trifluoromethyl-benzoylamide; sodium salt;
(c) (E)-2-(3-Chloro-phenyl)-ethenesulfonic acid 4-fluoro-2-trifluoromethyl-benzoylamide; sodium salt;
(d) (E)-2-(2-Chloro-phenyl)-ethenesulfonic acid 4-fluoro-2-trifluoromethyl-benzoylamide; sodium salt;
(e) (E)-2-(4-Trifluoromethoxy-phenyl)-ethenesulfonic acid 4-fluoro-2-trifluoromethyl-benzoylamide; sodium salt;
(f) (E)-2-Phenyl-ethenesulfonic acid 4-fluoro-2-trifluoromethyl-benzoylamide; sodium salt;
(g) (E)-2-(4-Chloro-phenyl)-ethenesulfonic acid 4-fluoro-2-trifluoromethyl-benzoylamide; sodium salt; and
(h) (E)-2-(4-Trifluoromethyl-phenyl)-ethenesulfonic acid 4-fluoro-2-trifluoromethyl-benzoylamide; sodium salt.

Another embodiment of the invention are the compounds of formula I, wherein $R^6$ is trifluoromethyl and $R^7$ is methyl.

Such a compound may, for example, be:
(E)-2-Phenyl-ethenesulfonic acid 4-methyl-2-trifluoromethyl-benzoylamide.

Another embodiment of the invention are the compounds of formula I, wherein $R^6$ is trifluoromethyl and $R^7$ is trifluoromethyl.

Such compounds may, for example, be:
(a) (E)-2-(2,4-Dimethyl-phenyl)-ethenesulfonic acid 2,4-bis-trifluoromethyl-benzoylamide; sodium salt;
(b) (E)-2-(3-Methoxy-phenyl)-ethenesulfonic acid 2,4-bis-trifluoromethyl-benzoylamide; sodium salt;
(c) (E)-2-(2-Methoxy-phenyl)-ethenesulfonic acid 2,4-bis-trifluoromethyl-benzoylamide; sodium salt;
(d) (E)-2-(3-Chloro-phenyl)-ethenesulfonic acid 2,4-bis-trifluoromethyl-benzoylamide; sodium salt;
(e) (E)-2-(2-Chloro-phenyl)-ethenesulfonic acid 2,4-bis-trifluoromethyl-benzoylamide; sodium salt;
(f) (E)-2-Phenyl-ethenesulfonic acid 2,4-bis-trifluoromethyl-benzoylamide; sodium salt;
(g) (E)-2-(2,4-Difluoro-phenyl)-ethenesulfonic acid 2,4-bis-trifluoromethyl-benzoylamide; sodium salt; and (h) (E)-2-(4-Chloro-phenyl)-ethenesulfonic acid 2,4-bis-trifluoromethyl-benzoylamide; sodium salt.

Another embodiment of the invention are the compounds of formula I, wherein $R^6$ is methoxy and $R^7$ is chlorine. Such compounds may, for example, be:

(a) (E)-2-(3-Methoxy-phenyl)-ethenesulfonic acid 4-chloro-2-methoxy-benzoylamide; sodium salt;
(b) (E)-2-Phenyl-ethenesulfonic acid 4-chloro-2-methoxy-benzoylamide; sodium salt; and
(c) (E)-2-(3-Chloro-phenyl)-ethenesulfonic acid 4-chloro-2-methoxy-benzoylamide; sodium salt.

Another embodiment of the invention are the compounds of formula I, wherein $R^6$ is methoxy and $R^7$ is bromine. Such a compound is for example:

(E)-2-Phenyl-ethenesulfonic acid 4-bromo-2-methoxy-benzoylamide.

Another embodiment of the invention are the compounds of formula I, wherein $R^6$ is methoxy and $R^7$ is fluorine. Such a compound may, for example, be:

(E)-2-Phenyl-ethenesulfonic acid 4-fluoro-2-methoxy-benzoylamide.

Another embodiment of the invention are the compounds of formula I, wherein $R^6$ is methoxy and $R^7$ is trifluoromethyl. Such a compound may, for example, be:

(E)-2-Phenyl-ethenesulfonic acid 2-methoxy-4-trifluoromethyl-benzoylamide.

Another embodiment of the invention is a process for the preparation of the compounds of formula I, comprising the steps of:

a) reacting a compound of formula II:

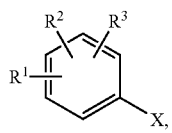

formula II wherein $R^1$, $R^2$ and $R^3$ have the significance given previously for formula I and X is iodine or bromine, with ethenesulfonic acid (1,1,3,3-tetramethyl-butyl)-amide:

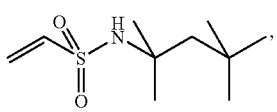

to obtain the compounds of formula IIIa:

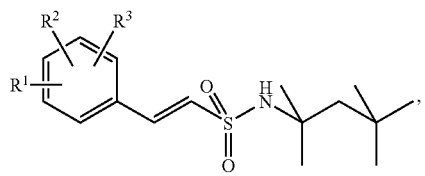

formula IIIa wherein $R^1$, $R^2$ and $R^3$ have the significance given previously for formula I, b) cleaving the 1,1,3,3-tetramethyl-butyl group of the compounds of formula IIIa to obtain the free sulfonamides of formula IVa:

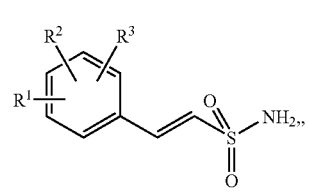

formula IVa wherein $R^1$, $R^2$ and $R^3$ have the significance given previously for formula I, and c) reacting the sulfonamides of formula IVa with the benzoic acid of formula XI:

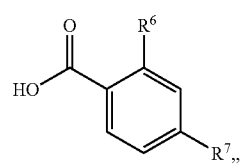

formula XI which is activated before, and wherein $R^6$ and $R^7$ have the significance given previously for formula I; to obtain the compounds of formula Ia,

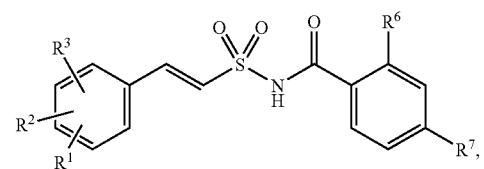

formula Ia wherein $R^1$, $R^2$, $R^3$, $R^6$ and $R^7$ have the significance given previously for formula I.

Another embodiment of the invention is a process for the preparation of the compounds of formula I, comprising the steps of:

a) reacting a compound of formula V:

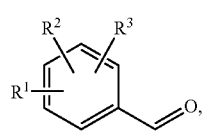

formula V wherein $R^1$, $R^2$ and $R^3$ have the significance given previously for formula I, with N-(1,1,3,3-tetramethyl-butyl)-methanesulfonamide:

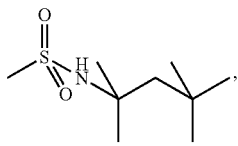

to obtain the compounds of formula VI:

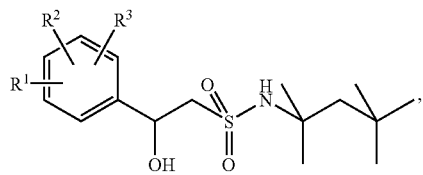

formula VI wherein $R^1$, $R^2$ and $R^3$ have the significance given previously for formula I, b) dehydrating the compounds of formula VI to obtain the compounds of formula IIIa:

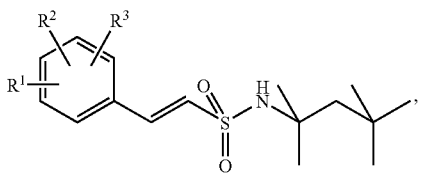

formula IIIa wherein $R^1$, $R^2$ and $R^3$ have the significance given previously for formula I, c) cleaving the 1,1,3,3-tetramethyl-butyl group of the compounds of formula IIIa to obtain the free sulfonamides of formula IVa:

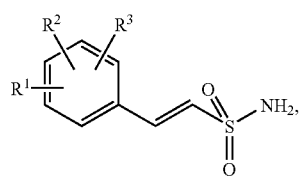

formula IVa wherein $R^1$, $R^2$ and $R^3$ have the significance given previously for formula I, and d) reacting the sulfonamides of formula IVa with the benzoic acid of formula XI:

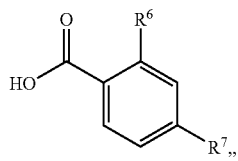

formula XI which is activated before, and wherein $R^6$ and $R^7$ have the significance given previously for formula I;

to obtain the compounds of formula Ia:

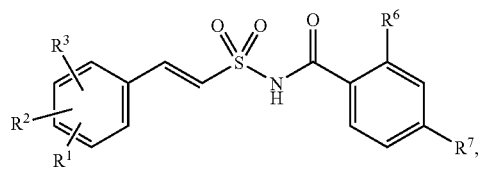

formula Ia wherein $R^1$, $R^2$, $R^3$, $R^6$ and $R^7$ have the significance given previously for formula I.

Another embodiment of the invention is a process for the preparation of the compounds of formula I, comprising the step of:

reacting a compound of formula IV:

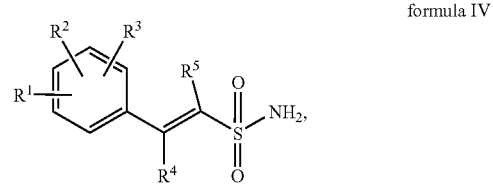

formula IV wherein $R^1$, $R^2$, $R^3$, $R^4$ and $R^5$ have the significance given previously for formula I, with the benzoic acid of formula XI:

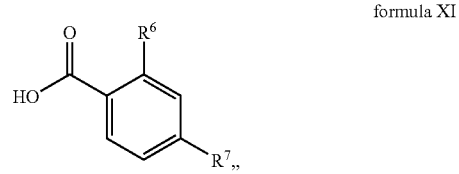

formula XI which is activated before, and wherein $R^6$ and $R^7$ have the significance given previously for formula I;

to obtain the compounds of formula I:

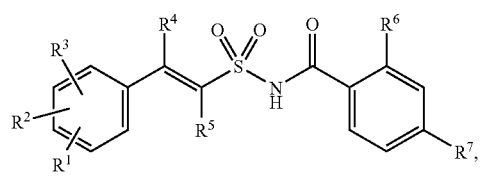

formula I wherein $R^1$, $R^2$, $R^3$, $R^4$, $R^5$, $R^6$ and $R^7$ have the significance given previously for formula I.

Another embodiment of the invention is a process for the preparation of the compounds of formula I, comprising the step of:

reacting a compound of formula VIII:

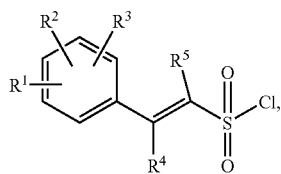

formula VIII wherein $R^1$, $R^2$, $R^3$, $R^4$ and $R^5$ have the significance given previously for formula I, with the benzamide of formula X:

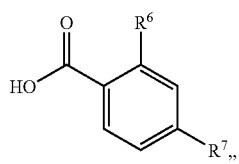

formula X wherein $R^6$ and $R^7$ have the significance given previously for formula I;

to obtain the compounds of formula I:

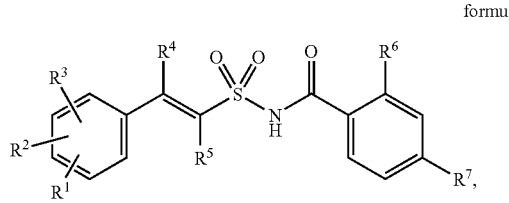

formula I wherein $R^1$, $R^2$, $R^3$, $R^4$, $R^5$, $R^6$ and $R^7$ have the significance given previously for formula I.

The compounds of formula I, or a pharmaceutically acceptable salt or ester thereof, which are subject of the present invention, may be prepared by any process known to be applicable to the preparation of chemically-related compounds. Such processes, when used to prepare a compound of the formula I, or a pharmaceutically-acceptable salt or ester thereof, are illustrated by the following representative schemes 1 to 5 and examples in which, unless otherwise stated, $R^1$, $R^2$, $R^3$, $R^4$, $R^5$, $R^6$ and $R^7$ have the significance given previously for formula I. Necessary starting materials are either commercially available or they may be obtained by standard procedures of organic chemistry. The preparation of such starting materials is described within the accompanying examples or in the literature cited below with respect to scheme 1 to 5. Alternatively necessary starting materials are obtainable by analogous procedures to those illustrated which are within the ordinary skill of an organic chemist.

The manufacture of the compounds of formula I varies according to the nature of $R^4$ and $R^5$ in formula I. The compounds of the present invention wherein $R^4$ and $R^5$ are hydrogen can be prepared according to the following scheme 1 and scheme 2, and are named Ia:

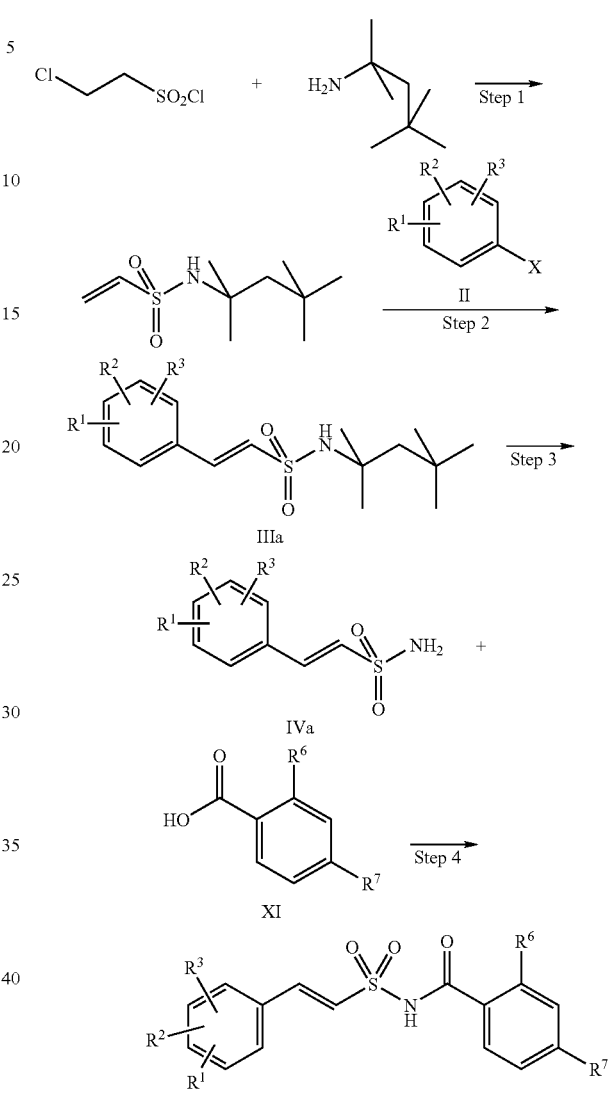

In scheme 1, $R^1$, $R^2$, $R^3$, $R^6$ and $R^7$ have the significance as given previously for formula I, X is iodine or bromine, and $R^4$ and $R^5$ are both hydrogen.

Step 1:

Step 1 of the reaction sequence (scheme 1) is a one step process involving two chemical transformation (sulfonylation and elimination) in which tert-octylamine is condensed with 2-chloroethane sulfonyl chloride using methods well known to someone skilled in the art, to give ethenesulfonic acid (1,1,3,3-tetramethyl-butyl)-amide. The reaction (sulfonylation and elimination) is typically carried out without solvent, or in solvents like dichloromethane, dichloroethane, acetonitrile, dioxane, tetrahydrofuran, dimethylformamide and mixtures thereof, at temperatures between −78° C. and 30° C. while in the presence or absence of a base such as triethylamine, diisopropylethylamine, potassium carbonate and potassium hydrogen carbonate.

Step 2:

In step 2, scheme 1 ethenesulfonic acid (1,1,3,3-tetramethyl-butyl)-amide is coupled with aryl halides, especially bromides and iodides, of the formula II, using methods well known to someone skilled in the art, e.g. palladium-mediated aryl coupling. The reaction is typically carried out in solvents like dimethylformamide, toluene, dioxane, tetrahydrofuran, and mixtures thereof, at temperatures between 80° C. and 175° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, bis-triphenylphosphinepalladium dichloride in conjunction with phosphine based ligands such as triphenylphosphine, tritolylphosphine and tributylphosphine.

Step 3:

In step 3, scheme 1 the obtained compounds of formula IIIa are converted into their corresponding primary sulfonamides of formula IVa, using methods well known to someone skilled in the art like the acidic cleavage of the N-protecting group. The reaction is typically carried out without solvent, or in solvents such as dichloromethane, dichloroethane, acetonitrile, dioxane, chloroform and mixtures thereof, at temperatures between −20° C. and 40° C. Typically used acids are trifluoroacetic acid, aqueous hydrogen chloride, anhydrous hydrogen chloride, sulphuric acid, trifluoromethane sulfonic acid.

Step 4:

Step 4 of the reaction sequence (scheme 1) is a two step process in which activation of the carboxylic group of the benzoic acid of formula XI is followed by acylation of IVa, yielding the acylsulfonamide derivatives of formula Ia. The first step (activation) is typically carried out without solvent, or in solvents like dichloromethane, dichloroethane, tetrahydrofuran, dioxane and mixtures thereof, at temperatures between 0° C. and 100° C. Typical methods used for the activation are chlorination or formation of an imidazolide. Typically used chlorinating reagents are thionylchloride, oxalyl chloride, phosphorus trichloride, phosphorus pentachloride, phosphorus oxychloride, N-chlorosuccinamide triphenylphosphine. A typically used imidazolination method is the reaction with NN'-carbonyl diimidazole (CDI). Other typically used activation methods include the use of activating agents such as 1-ethyl-3-(3'-dimethylaminopropyl)carbodiimide (EDCI), hydroxy-benzotriazole (HOBt) and the like. The second step (acylation) is typically carried out in solvents like dichloromethane, dichloroethane, acetonitrile, dioxane, tetrahydrofuran, chloroform, dimethylformamide and mixtures thereof, at temperatures between −10° C. and 100° C. Typically used bases are sodium hydride, potassium hydride, potassium carbonate, triethylamine, diisopropylethylamine, and DBU (1,8-diazabicyclo[5.4.0]undec-7-ene.

Scheme 2

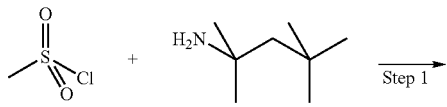

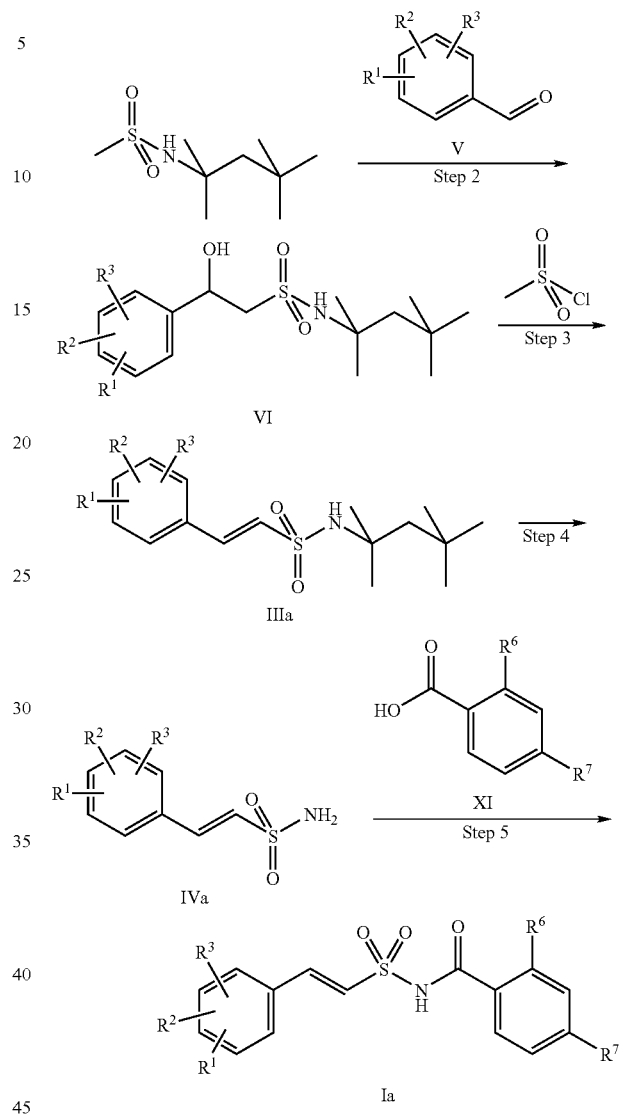

In scheme 2, $R^1$, $R^2$, $R^3$, $R^6$ and $R^7$ have the significance as given previously for formula I, and $R^4$ and $R^5$ are both hydrogen.

Step 1:

Step 1 of the reaction sequence (scheme 2) is a one step process in which tert-octylamine is condensed with methane sulfonyl chloride using methods well known to someone skilled in the art, to give methanesulfonic acid (1,1,3,3-tetramethyl-butyl)-amide. The reaction (sulfonylation) is typically carried out without solvent, or in solvents like dichloromethane, dichloroethane, acetonitrile, dioxane, tetrahydrofuran, dimethylformamide and mixtures thereof, at temperatures between −78° C. and 30° C. while in the presence or absence of a base such as triethylamine, diisopropylethylamine, potassium carbonate and potassium hydrogen carbonate.

Step 2:

In step 2, scheme 2 methanesulfonic acid (1,1,3,3-tetramethyl-butyl)-amide is coupled with aryl aldehydes of the formula V, using methods well known to someone skilled in the the art, to give secondary alcohol of the formula VI. The reaction is typically carried out in solvents like dioxane, tetrahydrofuran, and mixtures thereof, at temperatures between −78° C. and 30° C. while in the presence of a base such as n-butyl lithium, sec-butyl lithium and tert-butyl lithium.

Step 3:

In Step 3, scheme 2 the obtained compounds of formula VI are converted into their corresponding vinyl sulfonamides of formula IIIa (scheme 2) through the condensation with methane sulfonyl chloride using methods well known to someone skilled in the art. The reaction (sulfonylation) is typically carried out in solvents like dichloromethane, dichloroethane, acetonitrile, dioxane, tetrahydrofuran, dimethylformamide and mixtures thereof, at temperatures between −10° C. and 30° C. while in the presence or absence of a base such as triethylamine, diisopropylethylamine, potassium carbonate and potassium hydrogen carbonate. This is followed by spontaneous elimination to give vinyl sulfonamides of formula IIIa.

Step 4:

In step 4, scheme 2 the obtained compounds of formula IIIa are converted into their corresponding primary sulfonamides of formula IVa, using methods well known to someone skilled in the art like the acidic cleavage of the N-protecting group. The reaction is typically carried out without solvent, or in solvents such as dichloromethane, dichloroethane, acetonitrile, dioxane, chloroform and mixtures thereof, at temperatures between −20° C. and 40° C. Typically used acids are trifluoroacetic acid, aqueous hydrogen chloride, anhydrous hydrogen chloride, sulphuric acid, trifluoromethane sulfonic acid.

Step 5:

Step 5 of the reaction sequence (scheme 2) is a two step process in which activation of the carboxylic group of the benzoic acid of formula XI by acylation of IVa, yielding the acylsulfonamide derivatives of formula Ia. The first step (activation) is typically carried out without solvent, or in solvents like dichloromethane, dichloroethane, tetrahydrofuran, dioxane and mixtures thereof, at temperatures between 0° C. and 100° C. Typical methods used for the activation are chlorination or formation of an imidazolide. Typically used chlorinating reagents are thionylchloride, oxalyl chloride, phosphorus trichloride, phosphorus pentachloride, phosphorus oxychloride, N-chlorosuccinamide triphenylphosphine. A typically used imidazolination method is the reaction with N,N'-carbonyl diimidazole (CDI). Other typically used activation methods include the use of activating agents such as 1-ethyl-3-(3'-dimethylaminopropyl)carbodiimide (EDCI), hydroxy-benzotriazole (HOBt) and the like. The second step (acylation) is typically carried out in solvents like dichloromethane, dichloroethane, acetonitrile, dioxane, tetrahydrofuran, chloroform, dimethylformamide and mixtures thereof, at temperatures between −10° C. and 100° C. Typically used bases are sodium hydride, potassium hydride, potassium carbonate, triethylamine, diisopropylethylamine, and DBU (1,8-diazabicyclo [5.4.0] undec-7-ene.

Alternatively, instead of the tert-octyl amino protecting group in formulas IIa and VI, other suitable amino protecting groups like bis-paramethoxybenzyl or t-butyl (see Harada, H., et al, Bioorg. Med. Chem. 9 (2001) 2955–2968) can be used. The introduction is carried out using the same protocols as provided for step 1 of schemes 1 and 2 (see also Thompson, M. E., J. Org. Chem. 49 (1984) 1700–1703). The removal of the protecting group is carried out using the same protocols as provided for step 3 of scheme 1 and step 4 of scheme 2.

An alternative preparation of compounds IVa in scheme 1 or 2 is also described in Harada, H., et al, Bioorg. Med. Chem. 9 (2001) 2955–2968 and Hirooka, S., et al, Bull. Chem. Soc. Jap. 64 (1991) 1431–1433.

The manufacture of the compounds of formula I varies according to the nature of $R^4$ and $R^5$ in formula I. The compounds of the present invention wherein $R^4$ is hydrogen can be prepared according to the following scheme 3, and are named Ib:

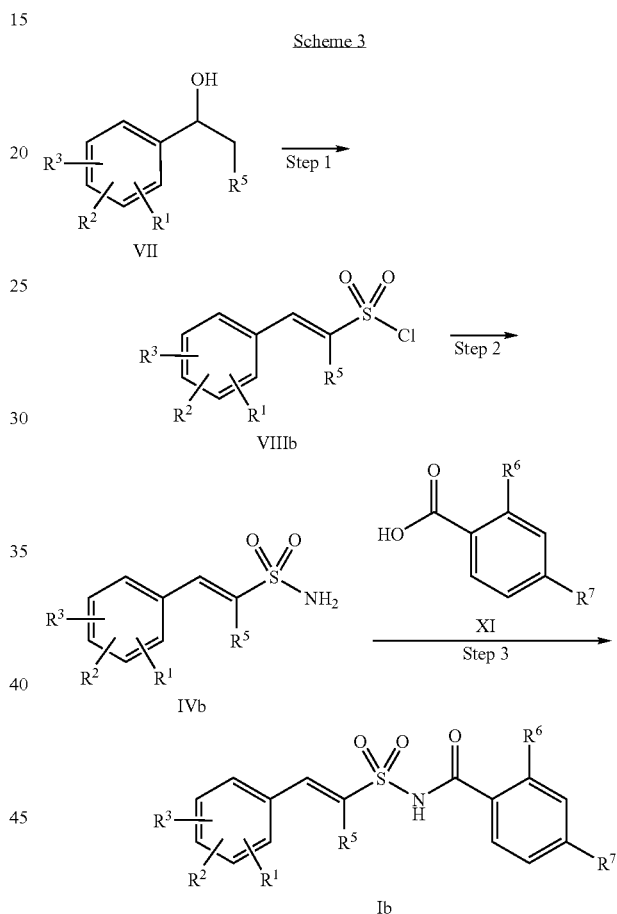

In scheme 3, $R^1$, $R^2$, $R^3$, $R^5$, $R^6$ and $R^7$ have the significance as given previously for formula I, and $R^4$ is hydrogen.

Step 1:

A preferred method for the synthesis of compounds of formula Ib starts from the corresponding benzyl alcohol of formula VII. Step 1 of the reaction sequence (scheme 3) is a sulfonylation of VII which is carried out e.g. with neat thionyl chloride (see e.g. Aramini, A., et al, J. Org. Chem. 68 (2003) 7911–7914) yielding the corresponding sulfonyl chlorides of formula VIIIb.

An alternative route to the sulfonyl chlorides of formula VIIIb starts from the corresponding styrene derivatives, which are sulfonylated by sulfuryl chloride ($SO_2Cl_2$) according to Harada, H., et al, Chem. Pharm. Bull. 49 (2001) 1593–1603.

Step 2:

Step 2, scheme 4, is the sulfonamide formation which is carried out by treatment of compounds of formula VIIIb with aqueous or ethanolic ammonia, or aqueous ammonium hydroxide performed e.g. in an etheral solvent such as tetrahydrofuran or diethylether (see. e.g. Harada, H., et al, Chem. Pharm. Bull. 49 (2001) 1593–1603 or U.S. Pat. No. 3,983,107A) to yield the styrylsulfonamides of formula IVb.

Step 3:

Step 3, scheme 4 is carried out analogously to Step 4, scheme 1 yielding the compounds of formula Ib.

The manufacture of the compounds of formula I varies according to the nature of $R^4$ and $R^5$ in formula I. The compounds of the present invention wherein $R^5$ is hydrogen can be prepared according to the following scheme 4, and are named Ic:

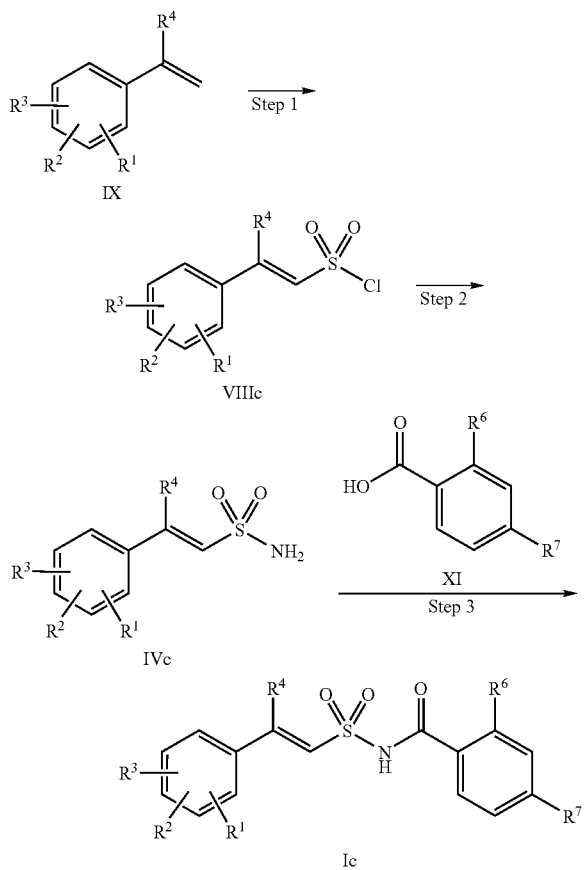

In scheme 4, $R^1$, $R^2$, $R^3$, $R^4$, $R^6$ and $R^7$ have the significance as given previously for formula I, and $R^5$ is hydrogen.

Step 1:

A preferred method for the synthesis of compounds of formula Ic starts from the corresponding styrenes of formula IX. Step 1 of the reaction sequence (scheme 4) is a sulfonylation typically carried out in DMF at 80° C. using e.g. sulfuryl chloride (see e.g. Harada, H., et al, Chem. Pharm. Bull. 49 (2001) 1593–1603 or Kameyama, M., et al, Bull. Chem. Soc. Jap. 61 (1988) 1231–1236) which yields the corresponding sulfonyl chlorides of formula VIIIc.

Step 2:

Step 2, scheme 4, is the sulfonamide formation which is carried out by treatment of compounds of formula VIIIc with aqueous ammonium hydroxide or aqueous ammonia performed e.g. in an etheral solvent such as tetrahydrofuran or diethylether (see. e.g. Harada, H. et al, Chem. Pharm. Bull. 49 (2001) 1593–1603 or U.S. Pat. No. 3,983,107A) yielding the styrylsulfonamides of formula IVc.

Step 3:

Step 3, scheme 4 is carried out analogously to Step 4, scheme 1 yielding the compounds of formula Ic.

Some sulfonamides of formula IV, wherein both $R^4$ and $R^5$ are alkyl, are known from WO 94/27979 and are prepared from 2-bromo-1,2-dialkyl-styrenes. They can be used for the preparation of compounds of formula I according to the respective last acylation steps of schemes 1 to 4. Or the sulfonamides of formula IV, wherein both $R^4$ and $R^5$ are alkyl, can be prepared according to the procedure of Harada, H. et al, Chem. Pharm. Bull. 49 (2001) 1593–1603, starting from the corresponding 1,2-dialkyl-styrenes.

Alternatively to schemes 1 to 4 the compounds of formula I can be prepared according to the following reaction sequence shown in scheme 5:

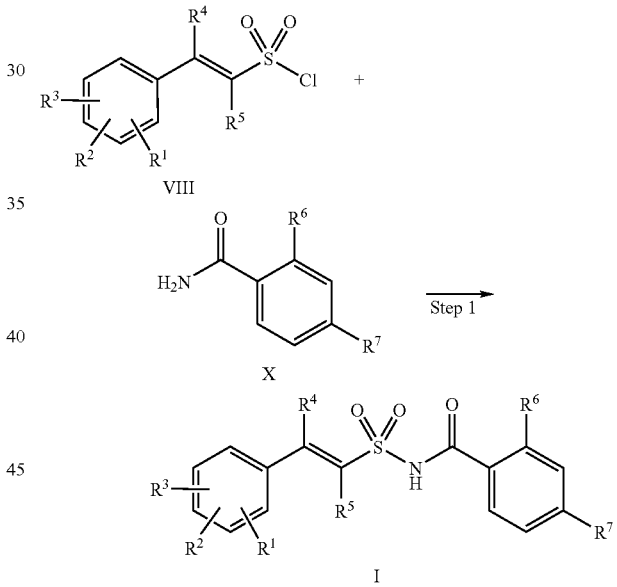

In scheme 5, $R^1$, $R^2$, $R^3$, $R^4$, $R^5$, $R^6$ and $R^7$ have the significance as given previously for formula I, and $R^4$ is hydrogen.

Step 1:

In step 1, scheme 5, the sulfonyl chlorides of formula IX are reacted with the benzamide of formula X in a N-sulfonylation reaction to yield the compounds of formula I. The reaction is carried e.g. in solvents like tetrahydrofuran or dimethylformamide, at temperatures between −80° C. and 50° C. in the presence of a base like lithium diisopropylamide, sodium hydride or potassium hydride (e.g. according to Beers, S. A., et al, Bioorg. Med. Chem. 5 (1997) 779–786; U.S. Pat. No. 4,157,257A; Horne, S., et al, J. Chem. Soc. Chem. Commun. 15 (1991) 1046–1048, Borthwick, A. D.; et al, J. Med. Chem. 43 (2000) 4452–4464 or Boger, D. L., et al, J. Org. Chem. 55 (1990) 1379–1390). The sulfonyl chlorides of formula IX are either prepared according to scheme 3, step 1 and scheme 4, step 1 or they can be prepared from the corresponding styrene derivatives using a) sulfur trioxide and phosphorus pentachloride (see e.g. Matier, W. L., et al., J. Med. Chem., 17 (1974) 549–552 or U.S. Pat. No. 3,983,107A), b) sulfuryl chloride ($SO_2Cl_2$) (see e.g. Harada, H., et al, Chem. Pharm. Bull. 49 (2001) 1593–1603 or Reddy, M. V., et al, Org. Prep. Proced. Int., 23 (1991) 633–638 or c) thionyl chloride ($SOCl_2$) (see e.g. Reddy, M. V., et al, Phosphorus, Sulfur Silicon Relat. Elem. 53 (1990) 285–290). Alternatively the sulfonyl chlorides of formula IX can be prepared from the aldehydes of formula VI according to the procedure of Wipf, P., et al Bioorg. Med. Chem. Lett. 11 (2001) 313–317.

Pharmaceutical compositions containing a compound of the present invention or a pharmaceutically acceptable salt or ester thereof and a pharmaceutically acceptable carrier are an object of the present invention, as is a process for their production, which comprises bringing one or more compounds of the present invention and/or pharmaceutically acceptable salts or esters and, if desired, one or more other therapeutic substances into a galenical administration form together with one or more pharmaceutically acceptable carriers.

An embodiment of the invention is a pharmaceutical composition, containing one or more compounds according to formula I, together with pharmaceutically acceptable excipients.

Another embodiment of the invention is a pharmaceutical composition, containing one or more compounds according to formula I, for the inhibition of tumor growth.

Another embodiment of the invention is a pharmaceutical composition, containing one or more compounds according to formula I, for the treatment of cancer.

Another embodiment of the invention is a pharmaceutical composition, containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of cancer.

Another embodiment of the invention is the use of the compounds of formula I as anti-proliferating agents.

Another embodiment of the invention is the use of one or more compounds of formula I for the treatment of cancer.

Pharmacological Activity

The compounds of formula I and their pharmaceutically acceptable salts or esters possess valuable pharmacological properties. It has been found that said compounds show anti-proliferative activity. Consequently the compounds of the present invention are useful in the therapy and/or prevention of proliferative diseases such as cancer. The activity of the present compounds as anti-proliferative agents is demonstrated by the following biological assay:

Viability Assay in HCT 116 Cells

A viability assay was performed using the CellTiter-Glo® Luminescent Cell Viability Assay (see Promega Corporation's Technical Bulletin No. 288, pp. 1–11 [revised 2/04] which is hereby incorporated by reference in its entirety). This assay is a homogeneous method of determining the number of viable cells in culture based on quantitation of the ATP present, an indicator of metabolically active cells. The assay is designed for use with multiwell formats, making it ideal for automated high-throughput screening (HTS), cell proliferation and cytotoxicity assays. The homogeneous assay procedure involves adding a single reagent (containing luciferase, luciferan substrate, and buffer) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The above-referenced assay generates a "glow-type" luminescent signal, produced by the luciferase reaction, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

HCT 116 cells (human colon carcinoma, ATCC-No. CCl-247) were cultivated in RPMI 1640 medium with GlutaMAX™ I (cell culture media that contains L-Alanyl-L-Glutamine [a stabilized a form/source of L-Glutamine] from Invitrogen, Cat-No. 61870-010), 2.5% Fetal Calf Serum (FCS, Sigma Cat-No. F4135 (FBS)); 100Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the viability assay was done according to the instructions of the manufacturer. In brief: the cell-plate was equilibrated to room temperature for approximately 30 minutes and then reagent (containing luciferase, luciferan substrate, and buffer) was added. The contents were carefully mixed for 15 minutes to induce cell lysis. After 45 minutes the luminescent signal was measured in Victor 2, (scanning multiwell spectrophotometer, Wallac).

Details:
  1st. day:
  Medium: RPMI 1640 with cell culture media containing L-Alanyl-L-Glutamine [GlutaMAX™ I (Invitrogen, Cat-No. 61870), 5% FCS (Sigma Cat.-No. F4135), Pen/Strep (Invitrogen, Cat No. 15140.
  HCT116 (ATCC-No. CCl-247): 1000 cells in 60 µl per well of 384 well plate (Greiner 781098, µClear-plate white)
  After seeding incubate plates 24 h at 37° C., 5% $CO_2$ 2nd. Day: Induction (Treatment with Compounds, 10 Concentrations):

In order to achieve a final concentration of 30 µM as highest concentration 3.5 µl of 10 mM compound stock solution were added directly to 163 µl media. Then step e) of the dilution procedure described below, was followed.

In order to achieve the second highest to the lowest concentrations, a serial dilution with dilution steps of 1:3 was followed according to the procedure (a–e) as described here below:

a) for the second highest concentration add 10 µl of 10 mM stock solution of compound to 20 µl dimethylsulfoxide (DMSO)
b) dilute 8×1:3 (always 10 µl to 20 µl DMSO) in this DMSO dilution row (results in 9 wells with concentrations from 3333.3 µM to 0.51 µM)
c) dilute each concentration 1:47.6 (3,5 µl compound dilution to 163 µl media)
e) add 10 µl of every concentration to 60 µl media in the cell plate resulting in final concentration of DMSO: 0.3% in every well and resulting in 10 final concentration of compounds ranging from 30 µM to 0.0015 µM.

Each compound is tested in triplicate.
Incubate 120 h (5 days) at 37° C., 5% $CO_2$
Analysis:
Add 30 µl of reagent containing luciferase, luciferan substrate, and buffer per well,
shake 15 minutes at room temperature
incubate further 45 minutes at room temperature without shaking
Measurement:
Victor 2 scanning multiwell spectrophotometer (Wallac), Luminescence mode (0.5 sec/read, 477 nm)
Determine IC50 using a non-linear curve fit (XLfit® software [ID Business Solution Ltd., Guilford, Surrey, UK])

A significant inhibition of HCT 116 cell viability was detected, which is exemplified by the compounds shown in Table 1.

TABLE 1

| Examples | IC50 HCT 116 [µM] |
|---|---|
| 1-1 | 8.5 |
| 1-2 | 3.1 |
| 3-1 | 9.2 |
| 1-3, 1-4, 1-5, 1-7, 1-8, 1-9, 1-13, 1-14, 1-17, 1-20, 1-23, 1-26, 1-28, 1-30, 1-33, 1-35, 1-36, 1-39, 1-42, 1-43, 1-45, 2-1, 4-2, 4-4, 4-5, 4-8, 4-10, 4-13, 4-16, 4-17, 4-18, 4-21, 4-22, 4-25, 4-28, 4-31, 4-34, 4-35, 4-37, 4-40, 5-1, 5-2, 5-3, 5-4, 5-6, 6-1, 6-2, 6-3, 6-5, 6-6 | 0.5–15.0 |

The compounds according to this invention and their pharmaceutically acceptable salts or esters can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. For example, lactose, corn starch or derivatives thereof, talc, stearic acids or its salts and the like can be used as such carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical composition may comprise, for example, the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The following examples and references are provided to aid the understanding of the present invention, the true scope of which is set forth in the appended claims. It is understood that modifications can be made in the procedures set forth without departing from the spirit of the invention.

Experimental Procedures:

Starting Materials

Preparation of Ethenesulfonic acid (1,1,3,3-tetramethyl-butyl)-amide

Tert-octylamine (1.47 mol, 236.3 ml), triethylamine (0.49 mol, 68.3 ml) and dichloromethane (400 ml) were placed in a 3 neck flask under nitrogen and cooled to −18° C. A solution of 2-chloro-1-ethane sulfonyl chloride in dichloromethane (400 ml) was added in a dropwise fashion over 2 hours, the reaction temperature was maintained between −18 and −9° C. during the addition. The reaction was allowed to warm to room temperature (RT) over 1 hour then washed with 1N HCl (400 ml) followed by distilled water (2×200 ml). The organic layer was dried with $MgSO_4$ then concentrated to give a pale yellow oil. The oil was dried under vacuum at 50° C. to give ethenesulfonic acid (1,1,3,3-tetramethyl-butyl)-amide, 96.0 g (90% yield) as a pale yellow oil.

$^1$H-NMR (400 MHz; d$^6$-DMSO) 0.98 (9H, s), 1.27 (6H, s), 1.54 (2H, s), 5.84 (1H, d, J=9.8 Hz), 5.99 (1H, d, J=16.4 Hz), 6.72 (1H, dd, J=9.8, 16.4 Hz), 6.90 (1H, s).

Preparation of (E)-2-Phenyl-propene-1-sulfonic acid amide

A solution of sulfuryl chloride (5.25 mL, 65.38 mmol) in dimethylformamide (DMF, 100 mL) is treated with α-methylstyrene (5 mL, 38.46 mmol) at room temperature (RT). The resulting solution is heated to 80° C. for 30 min before cooling to RT. The mixture is poured into ice water (100 mL) and extracted with chloroform (3×50 mL). The organic phases are combined and washed with brine (2×30 mL), dried over MgSO$_4$, and solvent removed under reduced pressure to yield the crude sulfonyl chloride. The crude sulfonyl chloride is dissolved in tetrahydrofuran (THF, 100 mL) and treated with aqueous NH$_4$OH (28%, 8.02 mL, 57.69 mmol) and stirred for 16 h at RT. The mixture is acidified and extracted with ethyl acetate (3×30 mL). The organic phases are combined and washed with brine (3×30 mL), dried over MgSO$_4$ and the solvent removed in vacuo. After column chromatography (ethyl acetate/hexanes 1:9->2:1) 2-phenyl-propene-1-sulfonic acid amide can be isolated as a light brown solid. Yield 172 mg (2%)

MS: M=196.0 (API−) $^1$H-NMR (400 MHz, d$^6$ DMSO): 2.42 (s, 3H), 6.66 (s, 1H), 7.12 (br, 2H), 7.43 (m, 3H), 7.52 (m, 2H)

Preparation of (E)-1-Phenyl-propene-2-sulfonic acid amide

Phenyl-1-propanol (10.0 mL, 72.25 mmol) is added dropwise to thionyl chloride 42.0 ml, 570.03 mmol) over a period of 30 min. The solution is refluxed for 17 h and then cooled to room temperature (RT). Excess thionyl chloride is removed under reduced pressure and the crude material is dissolved in THF (60 mL). The mixture is cooled to 0° C. and treated with ammonia (2M solution in ethanol (EtOH), 72.0 mL, 144.00 mmol) and then warmed to RT and stirred for a further 3.5 h. The solvent is removed under reduced pressure and the residue partitioned between chloroform (200 mL) and water (100 mL). The organic phase is separated and washed with water (100 mL), brine (2×50 mL), dried over Na$_2$SO$_4$ and solvent removed in vacuo. After column chromatography (ethyl acetate/hexanes 1:2->2:1) 1-phenyl-propene-2-sulfonic acid amide can be isolated as a light brown solid. Yield 250 mg (2%)

MS: M=196.0 (API−) $^1$H-NMR (400 MHz, d$^6$ DMSO): 2.21 (s, 3H), 7.06 (br, 2H), 7.38 (m, 2H), 7.46 (m, 4H)

Final Products

Sodium Salt Formation

The final products, which were obtained according to the procedures described below (in Examples 1-1 to 6-6), were or can be converted to their sodium salts using the following procedure:

To a solution of the sulfonamide (1 eq., e.g. 1 mmol) (obtained according to the procedures described below (in Examples 1-1 to 6-6)) in tetrahydrofurane (e.g. 10 ml), 1 eq. (e.g. 1 mmol) sodium methoxide (25% solution in methanol) was added and the mixture was stirred at room temperature for 1 hour. The tetrahydrofurane was removed in vacuo and the residue suspended in diethyl ether (e.g. 50 to 100 ml) and heated to reflux four 1 hour, cooled down to room temperature filtered off and dried.

EXAMPLE 1-1

(E)-2-(4-Chloro-phenyl)-ethenesulfonic acid 2,4-dichloro-benzoylamide i) (E)-2-(4-Chloro-phenyl)-ethenesulfonic acid (1,1,3,3-tetramethyl-butyl)-amide Ethenesulfonic acid (1,1,3,3-tetramethyl-butyl)-amide (8.5 g, 38.8 mmol) and 4-chloroiodoanisole (7.87 g, 33.0 mmol) was dissolved in N,N-dimethylformamide (65 ml). Palladium acetate (139 mg, 0.62 mmol) and triphenylphosphine (357 mg, 1.36 mmol) was added to the reaction followed by triethylamine (12.5 ml, 89.3 mmol). The reaction was flushed with nitrogen and heated at 140° C. for 16 hours. The reaction was cooled to room temperature and quenched with 1N HCl (250 ml). The aqueous solution was extracted with ethyl acetate (3×200 ml). The organic solution was dried over MgSO$_4$, filtered and concentrated in vacuo to afford a solid. The solid was dissolved in dichloromethane and purified by dry flash chromatography (SiO$_2$, heptane to 1:1 heptane: ethyl acetate). The fractions were combined to afford (E)-2-(4-chloro-phenyl)-ethenesulfonic acid (1,1,3,3-tetramethyl-butyl)-amide (5.0 g, 46% yield).

MS: M=681 (ESI+, 2M+Na) $^1$H-NMR (250 MHz; CDCl$_3$): 1.04 (9H, s), 1.42 (6H, s), 1.62 (2H, s), 4.29 (1H, br s), 6.75–6.81 (1H, d, J=15.4 Hz), 7.35–7.43 (5H, m).

ii) (E)-2-(4-Chloro-phenyl)-ethenesulfonic acid amide

To (E)-2-(4-chloro-phenyl)-ethenesulfonic acid (1,1,3,3-tetramethyl-butyl)-amide (5.0 g, 15.2 mmol) in dichloromethane (10 ml) was added trifluoroacetic acid (10 ml) and the mixture was stirred for 15 min. The mixture was concentrated in vacuo to afford a solid. The solid was washed with dichloromethane (5 ml) and heptane (150 ml). The resultant solid was collected by suction filtration. The solid was dried under vacuum at room temperature to afford (E)-2-(4-chloro-phenyl)-ethenesulfonic acid amide (2.95 g, 89%).

$^1$H-NMR (250 MHz; d$^4$-MeOD): 7.13–7.20 (1H, d, J=15.5 Hz), 7.40–7.48 (3H, m), 7.58–7.62 (2H, m).

iii) (E)-2-(4-Chloro-phenyl)-ethenesulfonic acid 2,4-dichloro-benzoylamide

To a solution of (E)-2-(4-chloro-phenyl)-ethenesulfonic acid amide (65 mg, 0.3 mmol) in 1,4-dioxane (1.5 ml) was added potassium carbonate (83 mg, 0.6 mmol) followed by 2,4-dichlorobenzoyl chloride (63 μL, 0.45 mmol). The reaction was heated at 80° C. for 16 hours then allowed to cool to room temperature whereupon 1N HCl (2 ml) was added. The mixture was extracted with ethyl acetate (2 ml), the organics were dried with MgSO$_4$ and washed with ethyl acetate (0.4 ml). The mixture was concentrated in vacuo and the resultant residue was purified by preparative HPLC to afford (E)-2-(4-chloro-phenyl)-ethenesulfonic acid 2,4-dichloro-benzoylamide (33.6 mg, 29%).

MS: M=390.0 (ESI+, M+H) $^1$H-NMR (250 MHz; d$^4$-MeOD): 7.36–7.42 (1H, d, J=15.4 Hz), 7.44–7.61 (5H, m), 7.68–7.77 (3H, m).

EXAMPLES 1-2 TO 1-42

The following examples 1-2 to 1-42 were prepared in an analogous manner as described for example 1-1 using the appropriate starting material:

| Example No. | Systematic Name | MS(ESI+, M+H) | $^1$H-NMR |
|---|---|---|---|
| 1-2 | (E)-2-Phenyl-ethenesulfonic acid 2,4-dichloro-benzoylamide | 356.0 | (400MHz, d$^6$-DMSO): 7.48(m, 3H), 7.53(dd, 1H), 7.54(d, J=15.4Hz, 1H), 7.61(d, 1H), 7.68(d, J=15.4Hz, 1H), 7.74(d, 1H), 7.81(m, 2H), 12.63(br, 1H) |
| 1-3 | (E)-2-(4-Trifluoromethyl-phenyl)-ethenesulfonic acid 2,4-dichloro-benzoylamide | 424.0 | (400MHz, d$^6$-DMSO): 7.53(dd, 1H), 7.63(d, 1H), 7.74(d J=15.0Hz, 1H), 7.75(d, 1H), 7.78(d J=15.0Hz, 1H), 7.84(d, 2H), 8.05(d, 2H), 12.72(br, 1H) |
| 1-4 | (E)-2-(2,4-Dimethyl-phenyl)-ethenesulfonic acid 2,4-dichloro-benzoylamide | 384.0 | (400MHz, d$^6$-DMSO): 2.31(s, 3H), 2.38(s, 3H), 7.10(d, 1H), 7.14(d, 1H), 7.34(d, J=15.3Hz, 1H), 7.52(dd, 1H), 7.59(d, 1H), 7.67(d, 1H), 7.73(d, 1H), 7.82(d, J=15.3Hz, 1H), 12.57(br, 1H) |
| 1-5 | (E)-2-(2-Methoxy-phenyl)-ethenesulfonic acid 2,4-dichloro-benzoylamide | 386.0 | (400MHz, d$^6$-DMSO): 3.91(s, 3H), 7.04(ddd, 1H), 7.15(dd, 1H), 7.48(m, 2H), 7.53(dd, 1H), 7.59(d, 1H), 7.74(d, 1H), 7.78(dd, 1H), 7.84(d, J=15.5Hz, 1H), 12.56(br, 1H) |
| 1-6 | (E)-2-(3-Chlorophenyl)-ethenesulfonic acid 2,4-dichloro-benzoylamide | 390.0 | (400MHz, d$^6$-DMSO): 7.52(m, 3H), 7.61(d, 1H), 7.67(s, 2H), 7.74(d, 1H), 7.78(dd, 1H), 7.98(m, 1H), 12.68(br, 1H) |
| 1-7 | (E)-2-(2-Chlorophenyl)-ethenesulfonic acid 2,4-dichloro-benzoylamide | 390.0 | (400MHz, d$^6$-DMSO): 7.46(ddd, 1H), 7.53(m, 2H), 7.62(m, 2H), 7.69(d J=15.3Hz, 1H), 7.75(d, 1H), 7.96(d J=15.3Hz, 1H), 8.04(dd, 1H), 12.73(br, 1H) |
| 1-8 | (E)-2-(2,4-Difluoro-phenyl)-ethenesulfonic acid 2,4-dichloro-benzoylamide | 392.0 | (400MHz, d$^6$-DMSO): 7.25(ddd, 1H), 7.44(ddd, 1H), 7.54(dd, 1H), 7.58(d J=15.5Hz, 1H), 7.62(d, 1H), 7.69(d J=15.5Hz, 1H), 775(d, 1H), 8.07(ddd, 1H), 12.71(br, 1H) |
| 1-9 | (E)-2-(4-Trifluoromethoxyphenyl)-ethenesulfonic acid 2,4-dichloro-benzoylamide | 440.0 | (400MHz, d$^6$-DMSO): 7.46(d, 2H), 7.53(dd, 1H), 7.61(d J=15.5Hz, 1H), 7.62(d, 1H), 7.72(d J=15.5Hz, 1H), 7.75(d, 1H), 7.98(d, 2H), 12.65(br, 1H) |
| 1-10 | (E)-2-(3,4-Dichloro-phenyl)-ethenesulfonic acid 2,4-dichloro-benzoylamide | 425.0 | (400MHz, d$^6$-DMSO): 7.54(dd, 1H), 7.61(d, 1H), 7.70(d J=14.8Hz, 1H), 7.72(d, 1H), 7.73(d J=14.8Hz, 1H), 7.75(d, 1H), 7.84(dd, 1H), 8.21(d, 1H), 12.65(br, 1H) |
| 1-11 | (E)-2-(2-Fluoro-phenyl)-ethenesulfonic acid 2,4-dichloro-benzoylamide | 395.9 | (400MHz, d$^6$-DMSO): 12.69(br. s, 1H), 7.96(t, J=7.6Hz, 1H), 7.75(d, J=1.7Hz, 1H), 7.73(d, J=15.6Hz, 1H), 7.63–7.55(m, 3H), 7.53(dd, J=8.2, 1.8Hz, 1H), 7.39–7.30(m, 2H) |
| 1-12 | (E)-2-o-Tolyl-ethenesulfonic acid 2,4-dichloro-benzoylamide | 392.0 | (400MHz, d$^6$-DMSO): 12.61(br. s, 1H), 7.87(d, J=15.2Hz, 1H), 7.76(d, J=7.8Hz, 1H), 7.74(d, J=1.8Hz, 1H), 7.61(d, J=8.3Hz, 1H), 7.52(dd, J=8.3, 1.8Hz, 1H), 7.39(d, J=15.2Hz, 1H), 7.38(m, 1H), 7.33–7.26(m, 2H), 2.42(s, 3H) |
| 1-13 | (E)-2-(2-Dimethylamino-phenyl)-ethenesulfonic acid 2,4-dichloro-benzoylamide | 399.1 | (400MHz, d$^6$-DMSO): 12.56(br. s, 1H), 7.90(d, J=15.4Hz, 1H), 7.73–7.70(m, 2H), 7.59(d, J=8.1Hz, 1H), 7.54–7.51(m, 1H), 7.46–7.39(m, 2H), 7.17(d, J=8.1Hz, 1H), 7.07(t, J=7.2Hz, 1H) 2.72(s, 6H) |
| 1-14 | (E)-2-(3-Methoxy-phenyl)-ethenesulfonic acid 2-chloro-4-fluoro- | 370.3 | (400MHz, d$^6$-DMSO): 7.42(m, 1H, phenyl-6-H), 7.15(d, 1H, ethene), 7.00(d, 1H, ethene, J=15.30Hz, trans), 7.14(s, 1H, methoxyphenyl-2-H), 7.09(m, |

| Example No. | Systematic Name | MS(ESI+, M+H) | $^1$H-NMR |
|---|---|---|---|
| | benzoylamide; sodium salt | | 1H, phenyl-3-H), 6.95(m, 3H, phenyl-5-H, methoxyphenyl-4-H, methoxyphenyl-6-H), 6.76(m, 1H, methoxyphenyl-4-H), 3.63(s, 3H, methoxy) |
| 1-15 | (E)-2-(2-Methoxy-phenyl)-ethenesulfonic acid 2-chloro-4-fluoro-benzoylamide; sodium salt | 370.3 | (400MHz, d$^6$-DMSO): 7.39(m, 1H, phenyl-6-H), 7.22(m, 2H, methoxyphenyl-5-H, ethene), 7.11(d, 1H, ethene, J=15.5Hz, trans), 7.00(m, 3H, methoxyphenyl-6-H, methoxyphenyl, phenyl), 6.80(m, 2H, phenyl-3-H, methoxyphenyl), 3.72(s, 3H, methyl) |
| 1-16 | (E)-2-(3-Chlorophenyl)-ethenesulfonic acid 2-chloro-4-fluoro-benzoylamide; sodium salt | 374.2 | (400MHz, d$^6$-DMSO): 7.43(s, 1H, chlorophenyl-2-H), 7.38(m, 1H, phenyl-6-H), 7.32(m, 1H, chlorophenyl-4-H), 7.19(m, 3H, chlorophenyl-5-H, chlorophenyl-6-H, ethene), 6.96(m, 1H, ethene, J=16.24Hz, trans), 7.04(m, 1H, phenyl-3-H), 6.89(m, 1H, phenyl-5-H) |
| 1-17 | (E)-2-(2,4-Difluoro-phenyl)-ethenesulfonic acid 2-chloro-4-fluoro-benzoylamide; sodium salt | 376.2 | (400MHz, d$^6$-DMSO): 7.54(m, 1H, difluorophenyl-3-H), 7.35(m, 1H, phenyl-6-H), 7.15(d, 1H, ethene, J=15.70Hz, trans), 7.07(m, 1H, phenyl-3-H), 7.03(m, 2H, difluorophenyl-6-H, ethene), 6.89(m, 2H, difluorophenyl-5-H, phenyl-5-H) |
| 1-18 | (E)-2-(4-Chlorophenyl)-ethenesulfonic acid 2-chloro-4-fluoro-benzoylamide; sodium salt | 374.2 | (400MHz, d$^6$-DMSO): 7.57(m, 3H, chlorophenyl-2-H, chlorophenyl-6-H, phenyl-6-H), 7.42(m, 2H, chlorophenyl-3-H, chlorophenyl-5-H), 7.31(d, 1H, ethene), 7.15(d, 1H, ethene, J=15.70Hz, trans), 7.23(m, 1H, phenyl-3-H), 7.08(m, 1H, phenyl-5-H) |
| 1-19 | (E)-2-(4-Methoxy-phenyl)-ethenesulfonic acid 2-chloro-4-fluoro-benzoylamide; sodium salt | 370.3 | (400MHz, d$^6$-DMSO): 7.55(m, 1H, phenyl-6-H), 7.47(d, 2H, methoxyphenyl-2-H, methoxyphenyl-6-H), 7.23(m, 1H, ethene), 7.12(m, 3H, phenyl-3-H, phenyl-5-H, ethene), 6.94(d, 2H, methoxyphenyl-3-H, methoxyphenyl-5-H), 3.77(s, 3H, methoxy) |
| 1-20 | (E)-2-(2,4-Dimethyl-phenyl)-ethenesulfonic acid 4-fluoro-2-trifluoromethyl-benzoylamide; sodium salt | 402.3 | (400MHz, d$^6$-DMSO): 7.50(m, 1H, phenyl-6-H), 7.34(m, 2H, phenyl-3-H, phenyl-5-H), 7.28(m, 2H, dimethylphenyl-6-H, ethene), 7.04(d, 1H, ethene, J=16.05Hz, trans), 6.95(m, 2H, dimethylphenyl-3-H, dimethylphenyl-5-H), 2.22(s, 3H, methyl), 2.18(s, 3H, methyl) |
| 1-21 | (E)-2-(3-Methoxy-phenyl)-ethenesulfonic acid 4-fluoro-2-trifluoromethyl-benzoylamide; sodium salt | 404.3 | (400MHz, d$^6$-DMSO): 7.40(m, 1H, phenyl-6-H), 7.23(m, 2H, phenyl-3-H, phenyl-5-H), 7.10(m, 2H, methoxyphenyl-5-H, ethene), 6.95(d, 1H, ethene, J=15.65Hz, trans), 6.90(m, 2H, methoxyphenyl-2-H, methoxyphenyl-6-H), 6.72(m, 1H, methoxyphenyl-4-H), 3.59(s, 3H, methoxy) |
| 1-22 | (E)-2-(3-Chlorophenyl)-ethenesulfonic acid 4-fluoro-2-trifluoromethyl-benzoylamide; sodium salt | 408.2 | (400MHz, d$^6$-DMSO): 7.79(m, 2H, phenyl-6-H, chlorophenyl-2-H), 7.70(m, 1H, chlorophenyl-4-H), 7.62(m, 4H, phenyl-3-H, phenyl-5-H, chlorophenyl-5-H, chlorophenyl-6-H), 7.54(d, 1H, ethene), 7.35(d, 1H, ethene, J=15.25Hz, trans) |

| Example No. | Systematic Name | MS(ESI+, M+H) | ¹H-NMR |
|---|---|---|---|
| 1-23 | (E)-2-(2-Chlorophenyl)-ethenesulfonic acid 4-fluoro-2-trifluoromethyl-benzoylamide; sodium salt | 408.2 | (400MHz, d⁶-DMSO): 7.73(m, 1H, chlorophenyl-3-H), 7.63(m, 1H, phenyl-6-H), 7.53(m, 2H, chlorophenyl-6-H), 7.46(m, 2H, phenyl-3-H, phenyl-5-H), 7.40(m, 3H, chlorophenyl-4-H, chlorophenyl-5-H, ethene) |
| 1-24 | (E)-2-(4-Trifluoromethoxyphenyl)-ethenesulfonic acid 4-fluoro-2-trifluoromethyl-benzoylamide; sodium salt | 458.2 | (400MHz, d⁶-DMSO): 7.88(m, 2H, trifluoromethoxy-2-H, trifluoromethoxy-6-H), 7.81(m, 1H, phenyl-6-H), 7.63(m, 2H, phenyl-3-H, phenyl-5-H), 7.57(d, 2H, trifluoromethoxy-3-H, trifluoromethoxy-5-H), 7.52(d, 1H, ethene), 7.41(d, 1H, ethene, J=15.65Hz, trans) |
| 1-25 | (E)-2-(4-Chlorophenyl)-ethenesulfonic acid 4-fluoro-2-trifluoromethyl-benzoylamide; sodium salt | 408.2 | (400MHz, d⁶-DMSO): 7.35(m, 3H, phenyl-6-H, chlorophenyl-2-H, chlorophenyl-6-H), 7.21(m, 4H, phenyl-3-H, phenyl-5-H, chlorophenyl-3-H, chlorophenyl-5-H), 7.08(d, 1H, ethene), 6.94(d, 1H, ethene, J=16.10Hz, trans) |
| 1-26 | (E)-2-(2,4-Dimethyl-phenyl)-ethenesulfonic acid 2,4-bis-trifluoromethyl-benzoylamide; sodium salt | 452.3 | (400MHz, d⁶-DMSO): 7.75(d, 1H, phenyl-6-H), 7.67(s, 1H, phenyl-3-H), 7.49(d, 1H, phenyl-5-H), 7.18(m, 2H, dimethylphenyl-3-H, ethene), 6.92(d, 1H, ethene, J=15.25Hz, trans), 6.83(m, 2H, dimethylphenyl-5-H, dimethylphenyl-6-H), 2.10(s, 3H, methyl), 2.06(s, 3H, methyl) |
| 1-27 | (E)-2-(3-Methoxy-phenyl)-ethenesulfonic acid 2,4-bis-trifluoromethyl-benzoylamide; sodium salt | 454.3 | (400MHz, d⁶-DMSO): 7.96(d, 1H, phenyl-6-H), 7.89(s, 1H, phenyl-3-H), 7.72(d, 1H, phenyl-5-H), 7.31(m, 2H, methoxyphenyl-5-H, ethene), 7.18(d, 1H, ethene, J=15.70Hz, trans), 7.11(m, 2H, methoxyphenyl-2-H, methoxyphenyl-6-H), 6.93(d, 1H, methoxyphenyl-4-H), 3.79(s, 3H, methoxy) |
| 1-28 | (E)-2-(2-Methoxy-phenyl)-ethenesulfonic acid 2,4-bis-trifluoromethyl-benzoylamide; sodium salt | 454.3 | (400MHz, d⁶-DMSO): 8.01(d, 1H, phenyl-6-H), 7.94(s, 1H, phenyl-3-H), 7.77(d, 1H, phenyl-5-H), 7.56(d, 1H, methoxyphenyl-6-H), 7.51(d, 1H, ethene), 7.34(d, 1H, ethene, J=16.05Hz, trans), 7.41(t, 1H, methoxyphenyl-5-H), 7.13(d, 1H, methoxyphenyl-3-H), 7.04(t, 1H, methoxyphenyl-4-H), 3.92(s, 3H, methoxy) |
| 1-29 | (E)-2-(3-Chlorophenyl)-ethenesulfonic acid 2,4-bis-trifluoromethyl-benzoylamide; sodium salt | 458.2 | (400MHz, d⁶-DMSO): 8.75(d, 1H, phenyl-6-H), 7.68(s, 1H, phenyl-3-H), 7.52(d, 1H, phenyl-5-H), 7.42(s, 1H, chlorophenyl-2-H), 7.32(d, 1H, chlorophenyl-4-H), 7.21(m, 2H, chlorophenyl-5-H, chlorophenyl-6-H), 7.15(d, 1H, ethene), 6.99(d, 1H, ethene, J=15.70Hz, trans) |
| 1-30 | (E)-2-(2-Chlorophenyl)-ethenesulfonic acid 2,4-bis-trifluoromethyl-benzoylamide; sodium salt | 458.2 | (400MHz, d⁶-DMSO): 7.77(d, 1H, phenyl-6-H), 7.70(s, 1H, phenyl-3-H), 7.53(m, 2H, chlorophenyl-3-H, phenyl-5-H), 7.33(m, 2H, chlorophenyl-6-H), 7.19(m, 3H, chlorophenyl-4-H, chlorophenyl-5-H, ethene) |
| 1-31 | (E)-2-(2,4-Difluoro-phenyl)-ethenesulfonic acid 2,4-bis-trifluoromethyl- | 460.3 | (400MHz, d⁶-DMSO): 7.78(d, 1H, phenyl-6-H), 7.71(s, 1H, phenyl-3-H), 7.56(m, 2H, phenyl-5-H, difluorophenyl-3-H), 7.15(m, 2H, difluorophenyl-6-H, |

-continued

| Example No. | Systematic Name | MS(ESI+, M+H) | $^1$H-NMR |
|---|---|---|---|
| | benzoylamide; sodium salt | | ethene), 7.07(d, 1H, ethene, J=15.70Hz, trans), 6.97(m, 1H, difluorophenyl-5-H) |
| 1-32 | (E)-2-(4-Chlorophenyl)-ethenesulfonic acid 2,4-bis-trifluoromethyl-benzoylamide; sodium salt | 458.2 | (400MHz, d$^6$-DMSO): 7.73(d, 1H, phenyl-6-H), 7.66(s, 1H, phenyl-3-H), 7.49(d, 1H, phenyl-5-H), 7.36(d, 2H, chlorophenyl-2-H, chlorophenyl-6-H), 7.22(d, 2H, chlorophenyl-3-H, chlorophenyl-5-H), 7.08(d, 1H, ethene), 6.96(d, 1H, ethene, J=15.65Hz, trans) |
| 1-33 | (E)-2-(2-Hydroxy-phenyl)-ethenesulfonic acid 2,4-dichloro-benzoylamide | 370.0 | (500MHz, d$^6$-DMSO): 12.49(br. s, 1H), 10.55(s, 1H), 7.81(d, 15.4Hz, 1H), 7.74(d, 1.6Hz, 1H), 7.65(d, 7.9Hz, 1H), 7.59(d, 8.2Hz, 1H), 7.52(dd, 8.4Hz, 1.7Hz, 1H), 7.47(d, 15.4Hz, 1H), 7.31(t, 7.4Hz, 1H), 6.95(d, 8.1Hz, 1H), 6.87(d, 7.6Hz, 1H) |
| 1-34 | (E)-2-(4-Hydroxy-phenyl)-ethenesulfonic acid 2,4-dichloro-benzoylamide | 370.1 | (400MHz, d$^6$-DMSO): 12.45(br. s, 1H), 10.15(s, 1H), 7.73(d, 1.5Hz, 1H), 7.63(d, 8.6Hz, 2H), 7.58(d, 8.1Hz, 1H), 7.55(d, 15.6Hz, 1H), 7.52(dd, 8.8Hz, 1.7Hz, 1H), 7.23(d, 15.4Hz, 1H), 6.83(d, 8.6Hz, 2H) |
| 1-35 | (E)-2-(3-Hydroxy-phenyl)-ethenesulfonic acid 2,4-dichloro-benzoylamide | 370.1 | (400MHz, d$^6$-DMSO): 12.59(br. s, 1H), 9.71(s, 1H), 7.74(d, 1.7Hz, 1H), 7.60(d, 8.3Hz, 1H), 7.55(d, 15.2Hz, 1H), 7.52(dd, 8.4Hz, 1.4Hz, 1H), 7.40(d, 15.4Hz, 1H), 7.26(t, 7.7Hz, 1H), 7.20(d, 7.6Hz, 1H), 7.11(m, 1H), 6.89(dd, 7.9Hz, 1.4Hz, 1H) |
| 1-36 | (E)-2-(2,4,6-Trifluoro-phenyl)-ethenesulfonic acid 2,4-dichloro-benzoylamide; sodium salt | 431.9 | (400MHz, d$^6$-DMSO): 7.51(d, 8.31Hz, 1H), 7.47(d, 2.0Hz, 1H), 7.42(d, 16.2Hz, 1H), 7.29–7.36(m, 3H), 7.16(d, 15.4Hz, 1H) |
| 1-37 | (E)-2-(4-Trifluoromethyl-phenyl)-ethenesulfonic acid 2-chloro-4-fluoro-benzoylamide; sodium salt | 408.8 | (400MHz, d$^6$-DMSO): 7.78(d, J=8.8Hz, 2H), 7.73(d, J=8.8Hz, 2H), 7.59(td, J=6.5, 1.8Hz, 1H), 7.46(d, J=15.4Hz, 1H), 7.29–7.25(m, 2H), 7.15(m, 1H) |
| 1-38 | (E)-2-(2,4-Dimethyl-phenyl)-ethenesulfonic acid 2-chloro-4-fluoro-benzoylamide; sodium salt | 368.3 | (400MHz, d$^6$-DMSO): 7.56(t, J=7.2Hz, 1H), 7.42–7.34(m, 2H), 7.24(m, 1H), 7.17–7.01(m, 4H), 2.31(s, 3H), 2.27(s, 3H) |
| 1-39 | (E)-2-(4-Trifluoromethoxyphenyl)-ethenesulfonic acid 2-chloro-4-fluoro-benzoylamide; sodium salt | 424.2 | (400MHz, d$^6$-DMSO): 7.65(d, J=8.7Hz, 2H), 7.54(td, J=6.9, 1.1Hz, 1H), 7.33(d, J=8.7Hz, 2H), 7.26(d, J=15.7Hz, 1H), 7.23–7.19(m, 1H), 7.17(d, J=15.7Hz, 1H), 7.08–7.03(m, 1H) |
| 1-40 | (E)-2-(3,4-Dichloro-phenyl)-ethenesulfonic acid 2-chloro-4-fluoro-benzoylamide; sodium salt | 409.7 | (400MHz, d$^6$-DMSO): 8.12(s, 1H), 7.77(d, J=8.4Hz, 1H), 7.71(d, J=8.4Hz, 1H), 7.67–7.48(m, 4H), 7.31–7.25(m, 1H) |
| 1-41 | (E)-2-(3,5-Dichloro-phenyl)-ethenesulfonic acid 2-chloro-4-fluoro-benzoylamide; sodium salt | 409.7 | |

| Example No. | Systematic Name | MS(ESI+, M+H) | ¹H-NMR |
|---|---|---|---|
| 1-42 | (E)-2-(4-Trifluoromethyl-phenyl)-ethenesulfonic acid 4-fluoro-2-trifluoromethyl-benzoylamide; sodium salt | 442.2 | (400MHz, d⁶-DMSO): 7.77(d, J=8.2Hz, 2H), 7.73(d, J=8.2Hz, 2H), 7.62(td, J=6.6, 1.5Hz, 1H), 7.47–7.39(m, 3H), 7.25(d, J=15.3Hz, 1H) |

EXAMPLES 1-43 TO 1-45

Starting from the appropriate starting materials, the following examples 1-43 to 1-45 were prepared in an analogous manner as described for example 1-1, steps i) and ii), and using instead of step iii) the following alternative procedure described for example 1-43:

EXAMPLE 1-43

2-Phenyl-ethenesulfonic acid 4-chloro-2-fluoro-benzoylamide

To a solution of 2-phenyl-ethenesulfonic acid amide (500 mg, 2.7 mmol) in dioxane (25 ml) sodium hydride (197 mg, 55% dispersion in mineral oil) were added and the mixture was stirred at room temperature for 30 minutes. 4-Chloro-2-fluoro-benzoyl chloride (527 mg, 2.7 mmol) were added and the mixture was stirred at room temperature overnight. After addition of water (50 ml) the pH was adjusted to 7 with 1 N HCl and the mixture was extracted with ethyl acetate (3 times 50 ml). The combined organic phases were dried over Na2SO4 and concentrated in vacuo. Preparative HPLC (RP18, methanol-water-gradient) returned the title compound (730 mg, 79% yield) as a white solid.

MS: M=338.1 (ESI⁺) ¹H-NMR (400 MHz, d⁶-DMSO): 7.11 (td, 8.6 Hz, 2.5 Hz, 1H); 7.19 (d, 15.9 Hz, 1H); 7.27 (dd, 9.1 Hz, 2.5 Hz, 1H); 7.32 (d, 15.7 Hz, 1H); 7.34–7.43 (m, 3H); 7.51–7.57 (m, 2H)

EXAMPLES 1-44 TO 1-45

| Example No. | Systematic Name | MS(ESI+, M+H) | ¹H-NMR |
|---|---|---|---|
| 1-44 | (E)-2-Phenyl-ethenesulfonic acid 2,4-bis-trifluoromethyl-benzoylamide; sodium salt | 422.1 | (400MHz, d⁶-DMSO): 7.21(d, 15.4Hz, 1H); 7.30(d, 15.9Hz, 1H); 7.33–7.45(m, 3H); 7.55(d, 7.1Hz, 2H); 7.73(d, 8.1Hz, 1H); 7.91(s, 1H), 7.97(d, 7.9Hz, 1H) |
| 1-45 | (E)-2-Phenyl-ethenesulfonic acid 4-fluoro-2-trifluoromethyl-benzoylamide; sodium salt | 472.1 | (400MHz, d⁶-DMSO): 7.18(d, 15.7Hz, 1H); 7.29(d, 15.9Hz, 1H); 7.32–7.49(m, 5H); 7.54(d, 7.3Hz, 2H), 7.58–7.64(m, 1H) |

EXAMPLE 2-1

(E)-1-Phenyl-propene-2-sulfonic acid 2,4-dichloro-benzoylamide

Phenyl-propene-2-sulfonic acid amide is dissolved in dioxane followed by the addition of potassium carbonate and 2,4-dichlorobenzoyl chloride. The resulting solution is stirred in a sealed tube at 100° C. for 18.5 h, cooled to room temperature (RT) and partitioned between 1M HCl and ethyl acetate. The aqueous phase is separated and extracted with further portions of ethyl acetate. The organic fractions are combined, washed with brine, dried over MgSO4 and concentrated in vacuo. After flash column chromatography (dichloromethane) 1-phenyl-propene-2-sulfonic acid 2,4-dichlorobenzoylamide can be isolated as a colourless oil. Yield 55 mg (56%).

MS: M=370.0 (ESI+, M+H) ¹H-NMR (400 MHz, CDCl₃): 2.37 (s, 3H), 7.37 (dd, 1H), 7.45 (m, 6H), 7.70 (d, 1H), 7.87 (d, 1H), 8.86 (br, 1H)

EXAMPLE 3-1

(E)-2-Phenyl-propene-1-sulfonic acid 2,4-dichloro-benzoylamide (E)-2-Phenyl-propene-1-sulfonic acid amide is dissolved in dioxane followed by the addition of potassium carbonate and 2,4-dichlorobenzoyl chloride. The resulting solution is stirred in a sealed tube at 100° C. for 18.5 h, cooled to room temperature (RT) and partitioned between 1M HCl and ethyl acetate. The aqueous phase is separated and extracted with further portions of ethyl acetate. The organic fractions are combined, washed with brine, dried over MgSO4 and concentrated in vacuo. After flash column chromatography (dichloromethane) (E)-2-phenyl-propene-1-sulfonic acid 2,4-dichlorobenzoylamide can be isolated as a colourless oil. Yield 90 mg (80%).

MS: M=370.0 (ESI+, M+H) ¹H-NMR (400 MHz, CDCl₃): 2.64 (s, 3H), 6.75 (s, 1H), 7.37 (dd, 1H), 7.46 (m, 6H), 7.74 (d, 1H), 9.07 (br, 1H)

EXAMPLE 4-1

(E)-2-(2-Chloro-phenyl)-ethenesulfonic acid 4-bromo-2-chloro-benzoylamide; sodium salt i) (E)-2-(2-Chloro-phenyl)-ethenesulfonic acid (1,1,3,3-tetramethyl-butyl)-amide Ethenesulfonic acid (1,1,3,3-tetramethyl-butyl)-amide (10 g, 46 mmol) and 2-chloroiodoanisole (4.8 mL, 39.1 mmol) was dissolved in N,N-dimethylformamide (DMF) (75 mL). Palladium acetate (169 mg, 0.75 mmol) and triphenylphosphine (420 mg, 1.6 mmol) was added to the reaction mixture followed by triethylamine (14.7 mL, 106 mmol). The reaction was flushed with nitrogen and heated at 140° C. for 16 hours. The reaction was cooled to room temperature whereupon 1N HCl (275 mL) was added. The aqueous solution was extracted with ethyl acetate (3×225 mL) and the combined organic solution was dried over MgSO$_4$, filtered and concentrated in vacuo to afford a solid. The solid was dissolved in dichloromethane and purified by dry flash chromatography (SiO$_2$, heptane to 1:1 heptane: ethyl acetate). The fractions were combined to afford (E)-2-(2-chloro-phenyl)-ethenesulfonic acid (1,1,3,3-tetramethyl-butyl)-amide (4.1 g, 32% yield).

$^1$H-NMR (250 MHz; d$^4$-MeOD): 1.23 (9H, s), 1.55 (6H, s), 1.85 (2H, s), 7.25 (1H, d, J=15.4 Hz), 7.57 (2H, m), 7.67 (1H, d, J=7.2 Hz) 7.93 (2H, m).

ii) (E)-2-(2-Chloro-phenyl)-ethenesulfonic acid amide (E)-2-(2-Chloro-phenyl)-ethenesulfonic acid (1,1,3,3-tetramethyl-butyl)-amide (4.55 g, 12.3 mmol) was stirred for 15 minutes in a 1:1 mixture of trifluoroacetic acid and dichloromethane (18 mL). The solution was concentrated in vacuo to afford a solid. The solid was washed with dichloromethane (5 mL) and heptane (150 mL) and was collected by suction filtration. The solid was dried under vacuum at room temperature to afford crude (E)-2-(2-chloro-phenyl)-ethenesulfonic acid amide (3.45 g) which was taken on to the next step without further purification.

$^1$H-NMR (250 MHz; d$^4$-MeOD): 7.42 (1H, d, J=15.5 Hz), 7.62 (2H, m), 7.72 (1H, d, J=7.4 Hz), 7.99 (1H, d, J=7.4 Hz) 8.07 (1H, d, J=15.5 Hz).

iii) 4-bromo-2-chloro-benzoyl chloride

4-Bromo-2-chloro-benzoic acid (0.64 g, 2.7 mmol) and DMF (50 µl) were added to dichloromethane (9 ml). Oxalyl chloride (0.47 ml, 5.4 mmol) was then added to the mixture and the resultant solution stirred at room temperature for 2 hours. The reaction was monitored to completion by LC-MS. The reaction was concentrated in vacuo to afford crude 4-bromo-2-chloro-benzoyl chloride.

iv) (E)-2-(2-Chloro-phenyl)-ethenesulfonic acid 2-bromo-4-chloro-benzoylamide; sodium salt Sodium hydride (60% dispersion in mineral oil) (36 mg, 0.9 mmol) was added to a solution of (E)-2-(2-chloro-phenyl)-ethenesulfonic acid amide (65 mg, 0.3 mmol) in 1,4-dioxane (1.5 mL) and the reaction mixture was shaken for 30 minutes. Crude 4-bromo-2-chloro-benzoyl chloride (114 mg, 0.45 mmol) in dioxane (0.5 mL) was added and the reaction mixture was shaken at room temperature for 18 hours. Water (0.1 mL) was added to the reaction mixture and the whole was concentrated in vacuo. The resultant residue was purified by preparative HPLC under neutral conditions to give (E)-2-(2-chloro-phenyl)-ethenesulfonic acid 4-bromo-2-chloro-benzoylamide; sodium salt (38 mg, 29% yield).

MS: M=370.7 (ESI+, M+H) $^1$H-NMR (400 MHz, d$^6$-DMSO): 7.63 (s, 1H, chlorophenyl-2-H), 7.60 (d, 1H, phenyl-5-H), 7.53 (m, 1H, chlorophenyl-4-H), 7.41 (m, 3H, chlorophenyl-5-H, chlorophenyl-6-H, ethene), 7.15 (m, 3H, phenyl-3-H, phenyl-6-H, ethene)

EXAMPLES 4-2 TO 4-42

The following examples 4-2 to 4-42 were prepared in an analogous manner as described for example 4-1 using the appropriate starting material:

| Example No. | Systematic Name | MS (ESI+, M+H) | $^1$H-NMR |
|---|---|---|---|
| 4-2 | (E)-2-(2-Chlorophenyl)-ethenesulfonic acid 4-chloro-2-methyl-benzoylamide; sodium salt | 370.7 | (400MHz, d$^6$-DMSO): 7.62(m, 1H, chlorophenyl-6-H), 7.48(d, 1H, phenyl-5-H), 7.38(m, 2H, chlorophenyl-6-H, ethene), 7.32(d, 1H, ethene, J=15.7Hz, trans), 7.26(m, 2H, chlorophenyl-4-H, chlorophenyl-5-H), 7.02(m, 2H, phenyl-3-H, phenyl-6-H), 2.30(s, 3H, methyl) |
| 4-3 | (E)-2-(3-Methoxy-phenyl)-ethenesulfonic acid 4-chloro-2-methyl-benzoylamide; sodium salt | 366.3 | (400MHz, d$^6$-DMSO): 7.35(d, 1H, phenyl-5-H), 7.15(m, 4H, phenyl-3-H, phenyl-6-H, methoxyphenyl-5-H, ethene), 6.94(m, 3H, methoxyphenyl-2-H, methoxyphenyl-6-H, ethene), 6.80(d, 1H, methoxyphenyl-4-H), 3.60(s, 3H, methoxy), 2.22(s, 3H, methyl) |
| 4-4 | (E)-2-(2-Methoxy-phenyl)-ethenesulfonic acid 4-chloro-2-methyl-benzoylamide; sodium salt | 366.3 | (400MHz, d$^6$-DMSO): 7.57(d, 1H, phenyl-5-H), 7.51(d, 1H, methoxyphenyl-6-H), 7.43(d, 1H, ethene), 7.33(m, 2H, methoxyphenyl-5-H, ethene, J=16.45Hz, trans), 7.14(d, 2H, phenyl-3-H, phenyl-6-H), 7.06(d, 1H, methoxyphenyl-3-H), 6.97(t, 1H, methoxyphenyl-4-H), 3.85(s, 3H, methoxy) |
| 4-5 | (E)-2-(3-Methoxy-phenyl)-ethenesulfonic acid 4-chloro-2-methoxy-benzoylamide; sodium salt | 382.3 | (400MHz, d$^6$-DMSO): 7.32(d, 1H, phenyl-3-H), 7.23(d, 1H, ethene), 7.11(d, 1H, ethene, J=15.70Hz), trans, 7.15(d, 2H, phenyl-6-H, methoxyphenyl-5-H), 6.88(d, 1H, phenyl-5-H), 6.79(m, 2H, methoxyphenyl-2-H, methoxyphenyl-6-H), 6.70(d, 1H, |

-continued

| Example No. | Systematic Name | MS (ESI+, M+H) | ¹H-NMR |
|---|---|---|---|
| 4-6 | (E)-2-(3-Chlorophenyl)-ethenesulfonic acid 4-chloro-2-methoxy-benzoylamide; sodium salt | 386.7 | (400MHz, d⁶-DMSO): 7.74(m, 1H, phenyl-6-H), 7.49(m, 2H, chlorophenyl-2-H, ethene), 7.38(m, 4H, chlorophenyl4-H, chlorophenyl-5-H, chlorophenyl-6-H, ethene), 6.96(s, 1H, phenyl-3-H), 6.89(d, 1H, phenyl-5-H), 3.73(s, 3H, methoxy) methoxyphenyl-4-H), 3.68(s, 3H, methoxy), 3.54(s, 3H, methoxy) |
| 4-7 | 2-(3-Methoxyphenyl)-ethenesulfonic acid 4-bromo-2-methyl-benzoylamide; sodium salt | 412.3 | (400MHz, d⁶-DMSO): 7.27(d, 1H, phenyl-5-H), 7.06(m, 4H, phenyl-3-H, phenyl-6-H, methoxyphenyl-5-H, ethene), 6.88(m, 3H, methoxyphenyl-2-H, methoxyphenyl-6-H, ethene), 6.67(d, 1H, methoxyphenyl-4-H), 3.54(s, 3H, methoxy), 2.17(s, 3H, methyl) |
| 4-8 | (E)-2-(2-Methoxy-phenyl)-ethenesulfonic acid 4-bromo-2-methyl-benzoylamide; sodium salt | 412.3 | (400MHz, d⁶-DMSO): 7.51(d, 1H, phenyl-5-H), 7.43(d, 1H, ethene, J=16.10Hz, trans), 7.32(m, 5H, phenyl-3-H, phenyl-6-H, methoxyphenyl-5-H, methoxyphenyl-6-H, ethene), 7.06(d, 1H, methoxyphenyl-3-H), 6.96(t, 1H, methoxyphenyl-4-H), 3.85(s, 3H, methoxy), 2.41(s, 3H, methyl) |
| 4-9 | (E)-2-(3-Chlorophenyl)-ethenesulfonic acid 4-bromo-2-methyl-benzoylamide; sodium salt | 416.2 | (400MHz, d⁶-DMSO): 7.43(s, 1H, chlorophenyl-2-H), 7.33(m, 2H, phenyl-5-H, chlorophenyl-4-H), 7.20(m, 3H, chlorophenyl-5-H, chlorophenyl-6-H, ethene), 6.97(d, 1H, ethene, J=15.7Hz, trans), 7.08(m, 2H, phenyl-3-H, phenyl-6-H), 2.21(s, 3H, methyl) |
| 4-10 | 2-(2-Chlorophenyl)-ethenesulfonic acid 4-bromo-2-methyl-benzoylamide; sodium salt | 416.2 | (400MHz, d⁶-DMSO): 7.63(m, 1H, chlorophenyl-3-H), 7.40(m, 3H, chlorophenyl-6-H, phenyl-5-H, ethene), 7.33(d, 1H, ethene), J=15.65Hz, trans, 7.26(m, 2H, chlorophenyl-4-H, chlorophenyl-5-H), 7.18(m, 2H, phenyl-3-H, phenyl-6-H), 2.31(s, 3H, methyl) |
| 4-11 | (E)-2-(3,4-Dichloro-phenyl)-ethenesulfonic acid 4-bromo-2-methyl-benzoylamide; sodium salt | 450.2 | (400MHz, d⁶-DMSO): 8.04(s, 1H, dichlorophenyl-2-H), 7.69(d, 1H, dichlorophenyl-6-H), 7.62(d, 1H, dichlorophenyl-5-H), 7.57(d, 1H, ethene), 7.50(d, 1H, ethene), J=15.65Hz, trans, 7.42(s, 1H, phenyl-3-H), 7.36(m, 2H, phenyl-5-H, phenyl-6-H), 2.24(s, 3H, methyl) |
| 4-12 | (E)-2-(3-Methoxy-phenyl)-ethenesulfonic acid 2-bromo-4-methyl-benzoylamide; sodium salt | 412.3 | (400MHz, d⁶-DMSO): 7.20(d, 1H, phenyl-5-H), 7.10(m, 3H, phenyl-3-H, methoxyphenyl-5-H, ethene), 6.95(d, 1H, ethene, J=16.10Hz, trans), 6.90(m, 3H, phenyl-6-H, methoxyphenyl-2-H, methoxyphenyl-6-H), 6.71(m, 1H, methoxyphenyl-4-H), 3.59(s, 3H, methoxy), 2.07(s, 3H, methyl) |
| 4-13 | (E)-2-(2-Methoxy-phenyl)-ethenesulfonic acid 2-bromo-4-methyl-benzoylamide; sodium salt | 412.3 | (400MHz, d⁶-DMSO): 7.38(d, 1H, phenyl-5-H), 7.31(d, 1H, ethane, J=16.05Hz, trans), 7.21(m, 4H, phenyl-3-H, methoxyphenyl-5-H, methoxyphenyl-6-H, ethene), 6.94(m, 2H, methoxyphenyl-3-H, phenyl-6-H), 6.85(t, 1H, methoxyphenyl-4-H), 3.73(s, 3H, methoxy), 2.14(s, 3H, methyl) |
| 4-14 | (E)-2-(3-Chlorophenyl)-ethenesulfonic | 416.2 | (400MHz, d⁶-DMSO): 7.38(s, 1H, chlorophenyl-2-H), 7.29(d, |

| Example No. | Systematic Name | MS (ESI+, M+H) | ¹H-NMR |
|---|---|---|---|
| | acid 2-bromo-4-methyl-benzoylamide; sodium salt | | 1H, chlorophenyl-4-H), 7.16(m, 5H, chlorophenyl-5-H, chlorophenyl-6-H, phenyl-3-H, phenyl-5-H, ethene), 6.92(d, 1H, ethene, J=15.7Hz, trans), 6.84(d, 1H, phenyl-6-H), 2.02(s, 3H, methyl) |
| 4-15 | (E)-2-(2-Chlorophenyl)-ethenesulfonic acid 2-bromo-4-methyl-benzoylamide; sodium salt | 416.2 | (400MHz, d⁶-DMSO): 7.74(m, 1H, chlorophenyl-3-H), 7.51(m, 2H, chlorophenyl-5-H, chlorophenyl-6-H), 7.40(m, 5H, chlorophenyl-4-H, phenyl-3-H, phenyl-5-H, ethene, ethene), 7.09(d, 1H, phenyl-6-H), 2.27(s, 3H, methyl) |
| 4-16 | (E)-2-(3,4-Dichloro-phenyl)-ethenesulfonic acid 2-bromo-4-methyl-benzoylamide; sodium salt | 450.2 | (400MHz, d⁶-DMSO): 7.65(d, 1H, dichlorophenyl-2-H), 7.43(d, 1H, dichlorophenyl-5-H), 7.37(m, 1H, dichlorophenyl-6-H), 7.20(m, 2H, phenyl-5-H, ethene), 6.96(d, 1H, ethene, J=15.65Hz, trans), 7.12(s, 1H, phenyl-3-H), 6.88(d, 1H, phenyl-6-H) |
| 4-17 | (E)-2-(4-Trifluoromethyl-phenyl)-ethenesulfonic acid 2-bromo-4-fluoro-benzoylamide; sodium salt | 454.2 | (400MHz, d⁶-DMSO): 7.57(d, 2H, trifluoromethyl-3-H, trifluoromethyl-5-H), 7.52(d, 2H, trifluoromethyl-2-H, trifluoromethyl-6-H), 7.33(m, 1H, phenyl-6-H), 7.25(d, 1H, ethene), 7.05(d, 1H, ethene, J=16.05Hz, trans), 7.19(m, 1H, phenyl-3-H), 6.93(m, 1H, phenyl-5-H) |
| 4-18 | (E)-2-(3-Methoxy-phenyl)-ethenesulfonic acid 2-bromo-4-fluoro-benzoylamide; sodium salt | 416.2 | (400MHz, d⁶-DMSO): 7.33(m, 1H, phenyl-6-H), 7.18(m, 1H, phenyl-3-H), 7.08(m, 2H, methoxyphenyl-6-H, ethene), 6.91(m, 4H, phenyl-5-H, methoxyphenyl-4-H, methoxyphenyl-5-H, ethene), 6.69(d, 1H, methoxyphenyl-3-H) |
| 4-19 | (E)-2-(2-Methoxy-phenyl)-ethenesulfonic acid 2-bromo-4-fluoro-benzoylamide; sodium salt | 416.2 | (400MHz, d⁶-DMSO): 7.46(m, 2H, phenyl-6-H, methoxyphenyl-6-H), 7.38(d, 1H, ethene, J=15.65Hz, trans), 7.34(m, 1H, phenyl-6-H), 7.26(m, 2H, methoxyphenyl-5-H, ethene), 7.08(m, 1H, phenyl-5-H), 7.00(d, 1H, methoxyphenyl-3-H), 6.91(t, 1H, methoxyphenyl-4-H), 3.79(s, 3H, methyl) |
| 4-20 | (E)-2-(3-Chlorophenyl)-ethenesulfonic acid 2-bromo-4-fluoro-benzoylamide; sodium salt | 420.2 | (400MHz, d⁶-DMSO): 7.77(s, 1H, chlorophenyl-2-H), 7.68(m, 2H, chlorophenyl-4-H, phenyl-6-H), 7.54(m, 4H, chlorophenyl-5-H, chlorophenyl-6-H, phenyl-3-H, ethene), 7.31(d, 1H ethene, J=16.05Hz, trans), 7.28(m, 1H, phenyl-5-H) |
| 4-21 | (E)-2-(2-Chlorophenyl)-ethenesulfonic acid 2-bromo-4-fluoro-benzoylamide; sodium salt | 420.2 | (400MHz, d⁶-DMSO): 7.51(m, 1H, chlorophenyl-5-H), 7.31(m, 3H, chlorophenyl-3-H, phenyl-6-H, ethene), 7.17(m, 4H, chlorophenyl-4-H, chlorophenyl-6-H, phenyl-3-H, ethene), 6.93(m, 1H, phenyl-5-H) |
| 4-22 | (E)-2-(4-Trifluoromethoxyphenyl)-ethenesulfonic acid 2-bromo-4-fluoro-benzoylamide; sodium salt | 470.2 | (400MHz, d⁶-DMSO): 7.55(d, 2H, trifluoromethoxyphenyl-2-H, trifluoromethoxyphenyl-6-H), 7.40(m, 1H, phenyl-6-H), 7.23(m, 4H, trifluoromethoxyphenyl-3-H, trifluoromethoxyphenyl-5-H, phenyl-3-H, ethene), 7.07(d, 1H, ethene, J=15.7Hz, trans), 7.00(m, 1H, phenyl-5-H) |

-continued

| Example No. | Systematic Name | MS (ESI+, M+H) | ¹H-NMR |
|---|---|---|---|
| 4-23 | (E)-2-(3,4-Dichloro-phenyl)-ethenesulfonic acid 2-bromo-4-fluoro-benzoylamide; sodium salt | 454.1 | (400MHz, d⁶-DMSO): 7.63(s, 1H, dichlorophenyl-2-H), 7.40(d, 1H, dichlorophenyl-5-H), 7.33(m, 2H, dichlorophenyl-6-H, phenyl-6-H), 7.17(m, 2H, phenyl-3-H, ethene), 6.94(m, 2H, phenyl-5-H, ethene) |
| 4-24 | (E)-2-(2,4-Dimethyl-phenyl)-ethenesulfonic acid 4-bromo-2-chloro-benzoylamide; sodium salt | 430.2 | (400MHz, d⁶-DMSO): 7.39(s, 1H, phenyl-3-H), 7.25(m, 3H, phenyl-5-H, phenyl-6-H, dimethylphenyl-6-H), 7.21(d, 1H, ethene), 6.97(d, 1H, ethene), 6.86(m, 2H, dimethylphenyl-3-H, dimethylphenyl-5-H), 2.14(s, 3H, methyl), 2.10(s, 3H, methyl) |
| 4-25 | (E)-2-(3-Methoxy-phenyl)-ethenesulfonic acid 4-bromo-2-chloro-benzoylamide; sodium salt | 432.2 | (400MHz, d⁶-DMSO): 7.32(s, 1H, phenyl-3-H), 7.21(bs, 2H, phenyl-5-H, phenyl-6-H), 7.06(m, 2H, methoxyphenyl-5-H, ethene), 6.92(d, 1H, ethene, J=15.7Hz, trans), 6.81(m, 2H, methoxyphenyl-2-H, methoxyphenyl-6-H), 6.68(m, 1H, methoxyphenyl-4-H), 3.55(s, 3H, methyl) |
| 4-26 | (E)-2-(2-Methoxy-phenyl)-ethenesulfonic acid 4-bromo-2-chloro-benzoylamide; sodium salt | 432.2 | (400MHz, d⁶-DMSO): 7.39(s, 1H, phenyl-3-H), 7.34(d, 1H, methoxyphenyl-6-H), 7.27(m, 3H, phenyl-5-H, phenyl-6-H, ethene), 7.12(d, 1H, ethene, J=15.70Hz, trans), 7.17(m, 1H, methoxyphenyl-5-H), 6.89(d, 1H, methoxyphenyl-3-H), 6.80(t, 1H, methoxyphenyl-4-H), 3.68(s, 3H, methyl) |
| 4-27 | (E)-2-(3-Chloro-phenyl)-ethenesulfonic acid 4-bromo-2-chloro-benzoylamide; sodium salt | 436.1 | (400MHz, d⁶-DMSO): 7.42(s, 1H, chlorophenyl-2-H), 7.34(s, 1H, phenyl-3-H), 7.31(d, 1H, phenyl-5-H), 7.19(m, 5H, chlorophenyl-4-H, chlorophenyl-5-H, chlorophenyl-6-H, phenyl-6-H, ethene), 6.95(d, 1H, ethene, J=15.3Hr, trans) |
| 4-28 | (E)-2-(2-Chloro-phenyl)-ethenesulfonic acid 4-bromo-2-chloro-benzoylamide; sodium salt | 436.1 | (400MHz, d⁶-DMSO): 7.51(m, 1H, chlorophenyl-3-H), 7.34(s, 1H, phenyl-3-H), 7.29(m, 2H, chlorophenyl-6-H, ethene), 7.22(bs, 2H, phenyl-5-H, phenyl-6-H), 7.16(m, 3H, chlorophenyl-4-H, chlorophenyl-5-H, ethene) |
| 4-29 | (E)-2-(3,4-Dichloro-phenyl)-ethenesulfonic acid 4-bromo-2-chloro-benzoylamide; sodium salt | 470.1 | (400MHz, d⁶-DMSO): 7.69(s, 1H, phenyl-3-H), 7.45(d, 1H, dichlorophenyl-5-H), 7.40(d, 2H, dichlorophenyl-2-H, dichlorophenyl-6-H), 7.28(s, 2H, phenyl-5-H, phenyl-6-H), 7.23(d, 1H, ethene), 7.00(d, 1H, ethene, J=15.65Hz, trans) |
| 4-30 | (E)-2-(3-Methoxy-phenyl)-ethenesulfonic acid 2,4-dimethyl-benzoylamide; sodium salt | 436.1 | (400MHz, d⁶-DMSO): 7.52(d, 1H, phenyl-6-H), 7.35(d, 1H, ethene, J=15.7Hz, trans), 7.29(t, 1H, methoxyphenyl-5-H), 7.10(m, 3H, methoxyphenyl-4-H, methoxyphenyl-6-H, ethene), 6.89(m, 3H, methoxyphenyl-2-H, phenyl-3-H, phenyl-5-H), 3.78(s, 3H, methoxy), 2.39(s, 3H, methyl), |
| 4-31 | (E)-2-(2-Methoxy-phenyl)-ethenesulfonic acid 2,4-dimethyl-benzoylamide; sodium salt | 345.9 | (400MHz, d⁶-DMSO): 7.37(m, 2H, methoxyphenyl-6-H, phenyl-6-H), 7.29(d, 1H, ethene, J=16.05Hz, trans), 7.19(m, 2H, methoxyphenyl-5-H, ethene), 6.92(s, 1H, methoxyphenyl-3-H), 6.83(t, 1H, methoxyphenyl-4-H), 6.75(m, 2H, phenyl-3-H, phenyl-5-H), |

-continued

| Example No. | Systematic Name | MS (ESI+, M+H) | $^1$H-NMR |
|---|---|---|---|
| 4-32 | (E)-2-(3-Chloro-phenyl)-ethenesulfonic acid 2,4-dimethyl-benzoylamide; sodium salt | 350.3 | 3.72(s, 3H, methoxy), 2.26(s, 3H, methyl), 2.11(s, 3H, methyl) (400MHz, d$^6$-DMSO): 7.52(s, 1H, chlorophenyl-2-H), 7.43(m, 2H, chlorophenyl-4-H, chlorophenyl-6-H), 7.32(m, 3H, chlorophenyl-5-H, phenyl-6-H, ethene), 7.05(d, 1H, ethene, J=15.65Hz, trans), 6.79(m, 2H, phenyl-3-H, phenyl-5-H), 2.30(s, 3H, methyl), 2.14(s, 3H, methyl) |
| 4-33 | (E)-2-(2-Chlorophenyl)-ethenesulfonic acid 2,4-dimethyl-benzoylamide; sodium salt | 350.3 | (400MHz, d$^6$-DMSO): 7.55(m, 1H, chlorophenyl-3-H), 7.33(m, 3H, chlorophenyl-6-H, phenyl-6-H, ethene), 7.26(d, 1H, ethene, J=15.7Hz, trans), 7.19(m, 2H, chlorophenyl-4-H, chlorophenyl-5-H), 6.71(m, 2H, phenyl-3-H, phenyl-5-H), 2.22(s, 3H, methyl), 2.06(s, 3H, methyl) |
| 4-34 | (E)-2-(3,4-Dichloro-phenyl)-ethenesulfonic acid 2,4-dimethyl-benzoylamide; sodium salt | 384.8 | (400MHz, d$^6$-DMSO): 7.61(s, 1H, dichlorophenyl-2-H), 7.38(d, 1H, dichlorophenyl-5-H), 7.31(m, 2H, dichlorophenyl-6-H, phenyl-6-H), 7.21(d, 1H, ethene), 6.90(d, 1H, ethene, J=16.45Hz, trans), 6.65(m, 2H, phenyl-3-H, phenyl-5-H), 2.16(s, 3H, methyl), 2.00(s, 3H, methyl) |
| 4-35 | (E)-2-(4-Trifluoromethyl-phenyl)-ethenesulfonic acid 4-bromo-2-methyl-benzoylamide; sodium salt | 442.3 | (400MHz, d$^6$-DMSO): 7.78(d, J=8.0Hz, 2H), 7.72(d, J=8.0Hz, 2H), 7.53(d, J=8.5Hz, 1H), 7.49(d, J=15.7Hz, 1H), 7.30(s, 1H), 7.28(d, J=8.5Hz, 1H), 7.24(d, J=15.7Hz, 1H), 2.41(s, 3H) |
| 4-36 | (E)-2-(4-Trifluoromethoxyphenyl)-ethenesulfonic acid 4-bromo-2-methyl-benzoylamide; sodium salt | 465.3 | (400MHz, d$^6$-DMSO): 7.69(d, J=8.4Hz, 2H), 7.52(d, J=8.1Hz, 1H), 7.37(d, J=15.6Hz, 1H), 7.36(d, J=8.4Hz, 2H), 7.30–7.25(m, 2H), 7.19(d, J=15.6Hz, 1H), 2.41(s, 3H) |
| 4-37 | (E)-2-(4-Trifluoromethoxyphenyl)-ethenesulfonic acid 2-bromo-4-methyl-benzoylamide; sodium salt | 465.3 | (400MHz, d$^6$-DMSO): 7.69(d, J=8.4Hz, 2H), 7.40–7.31(m, 5H), 7.20(d, J=15.7Hz, 1H), 7.08(d, J=8.0Hz, 1H), 2.27(s, 3H) |
| 4-38 | (E)-2-(4-Trifluoromethyl-phenyl)-ethenesulfonic acid 4-bromo-2-chloro-benzoylamide; sodium salt | 469.7 | (400MHz, d$^6$-DMSO): 7.79(d, J=8.0Hz, 2H), 7.73(d, J=8.0Hz, 2H), 7.56(s, 1H), 7.45(app. s, 2H), 7.45(d, J=15.7Hz, 1H), 7.26(d, J=15.7Hz, 1H) |
| 4-39 | (E)-2-(4-Trifluoromethoxyphenyl)-ethenesulfonic acid 4-bromo-2-chloro-benzoylamide; sodium salt | 485.7 | (400MHz, d$^6$-DMSO): 7.69(d, J=8.4Hz, 2H), 7.56(s, 1H), 7.44(app. s, 2H), 7.36(d, J=8.4Hz, 2H), 7.34(d, J=15.0Hz, 1H), 7.21(d, J=15.0Hz, 1H) |
| 4-40 | (E)-2-(4-Trifluoromethyl-phenyl)-ethenesulfonic acid 2,4-dimethyl-benzoylamide; sodium salt | 384.4 | (400MHz, d$^6$-DMSO): 7.77(d, J=8.2Hz, 2H), 7.72(d, J=8.2Hz, 2H), 7.53(m, 1H), 7.50(d, J=16.0Hz, 1H), 7.22(d, J=16.0Hz, 1H), 6.88(app. s, 2H), 2.40(s, 3H), 2.23(s, 3H) |
| 4-41 | (E)-2-(2,4-Dimethyl-phenyl)-ethenesulfonic | 344.4 | (400MHz, d$^6$-DMSO): 7.50(d, J=8.4Hz, 1H), 7.39(d, J=8.0Hz, 1H), 7.34(d, J=15.7Hz, 1H), |

| Example No. | Systematic Name | MS (ESI+, M+H) | $^1$H-NMR |
|---|---|---|---|
| | acid 2,4-dimethyl-benzoylamide; sodium salt | | 7.25(d, J=15.7Hz, 1H), 7.07–7.00(m, 2H), 6.89–6.86(m, 2H), 2.39(s, 3H), 2.31(s, 3H), 2.27(s, 3H), 2.23(s, 3H) |
| 4-42 | (E)-2-(4-Trifluoromethoxyphenyl)-ethenesulfonic acid 2,4-dimethyl-benzoylamide; sodium salt | 400.4 | (400MHz, d$^6$-DMSO): 7.68(d, J=8.4Hz, 2H), 7.52(d, J=8.4Hz, 1H), 7.39(d, J=16.1Hz, 1H), 7.35(d, J=8.4Hz, 2H), 7.17(d, J=16.1Hz, 1H), 6.88(app. s, 2H), 2.39(s, 3H), 2.23(s, 3H) |

EXAMPLE 5-1

(E)-2-Phenyl-ethenesulfonic acid 4-bromo-2-methoxy-benzoylamide

To a solution of 4-bromo-2-methoxy-benzoic acid (159 mg, 0.69 mmol) and 2-phenyl-ethenesulfonic acid amide (108 mg, 0.59 mmol) (which was prepared analogously to example 1-1 steps i) to iii) starting from iodoanisole) in dichloromethane (5 mL) and N,N-dimethylformamide (DMF) (2 mL) is added 1-ethyl-3-(3'-dimethylaminopropyl) carbodiimide (EDCI) (170 mg, 0.89 mmol) and 4-(dimethylamino)-pyridine (DMAP) (89 mg, 0.73 mmol) at RT. The mixture was stirred at RT for 20 h, and solvent removed under reduced pressure. The crude reaction mixture is partitioned between water (15 mL) and ethyl acetate (15 mL). The organic phase is separated and washed with aq. 1M HCl (4×10 mL), and the aqueous phases combined and back extracted with ethyl acetate (3×10 mL). The organic phases were combined and washed with water (15 mL), brine (2×10 mL) and dried (sodium sulfate) and concentrated in vacuo. After flash chromatography (CH$_2$Cl$_2$/MeOH 10:1) (E)-2-phenyl-ethenesulfonic acid 4-bromo-2-methoxy-benzoylamide can be isolated as a white solid. Yield 65 mg (24%)

MS: M=398.0 (ESI$^+$) $^1$H-NMR (400 MHz, d$^6$-DMSO): 11.76 (br. s, 1H) 7.79 (d, J=8.1 Hz, 2H), 7.64 (d, J=15.4 Hz, 1H), 7.50–7.45 (m, 4H), 7.42 (d, J=8.1 Hz, 1H), 7.36 (d, J=1.4 Hz, 1H), 7.22 (dd, J=8.2, 1.6 Hz, 1H), 3.87 (s, 3H)

EXAMPLES 5-2 TO 5-6

The following examples 5-2 to 5-6 were prepared in an analogous manner as described for example 5-1 using the appropriate starting material:

| Example No. | Systematic Name | MS (ESI+, M+H) | $^1$H-NMR |
|---|---|---|---|
| 5-2 | (E)-2-Phenyl-ethenesulfonic acid 4-methyl-2-trifluoromethyl-benzoylamide | 370.1 | (400MHz, d$^6$-DMSO): 12.56(br. s, 1H) 7.80–7.77(m, 2H), 7.66(d, J=15.6Hz, 1H), 7.64(m., 1H), 7.56(s, 2H), 7.51–7.45(m, 4H), 2.42(s, 3H) |
| 5-3 | (E)-2-Phenyl-ethenesulfonic acid 4-fluoro-2-methoxy-benzoylamide | 336.2 | (400MHz, CDCl$_3$): 10.08(br. s, 1H) 8.20(dd, J=8.8, 6.8Hz, 1H), 7.80(d, J=15.4Hz, 1H), 7.58–7.55(m, 2H), 7.48–7.40(m, 3H), 7.20(d, J=15.4Hz, 1H), 6.83(app. td, J=8.8, 2.3Hz, 1H), 6.75(dd, J=10.3, 2.3Hz, 1H), 4.05(s, 3H) |
| 5-4 | (E)-2-Phenyl-ethenesulfonic acid 2-bromo-4-chloro-benzoylamide | 402.0 | (400MHz, d$^6$-DMSO): 12.58(br. s, 1H) 7.86(d, J=1.7Hz, 1H), 7.82–7.79(m, 2H), 7.67(d, J=15.4Hz, 1H), 7.57–7.56(m, 2H), 7.52(d, J=15.4Hz, 1H), 7.50–7.45(m, 3H) |
| 5-5 | (E)-2-Phenyl-ethenesulfonic acid 4-chloro-2-trifluoromethyl-benzoylamide | 390.2 | (400MHz, d$^6$-DMSO): 12.70(br. s, 1H) 7.95(d, J=1.4Hz, 1H), 7.88(dd, J=8.3, 1.4Hz, 1H), 7.81–7.77(m, 2H), 7.73(d, J=8.3Hz, 1H), 7.67(d, J=15.4Hz, 1H), 7.53–7.45(m, 4H) |
| 5-6 | (E)-2-Phenyl-ethenesulfonic acid 2-methoxy-4-trifluoromethyl-benzoylamide | 384.2 | (400MHz, d$^6$-DMSO): 12.10(br. s, 1H) 7.80(dd, J=8.8, 2.3Hz, 2H), 7.66(d, J=15.4Hz, 1H), 7.64(d, J=7.8Hz, 1H), 7.51(d, J=15.4Hz, 1H), 7.50–7.45(m, 3H), 7.41(d, J=2.3Hz, 1H), 7.36(d, J=8.8Hz, 1H), 3.92(s, 3H) |

EXAMPLE 6-1

2-Phenyl-ethenesulfonic acid 4-chloro-2-methoxy-benzoylamide

A mixture of 4-chloro-2-methoxybenzoic acid (509 mg, 2.7 mmol) and CDI (443 mg, 2.7 mmol) in dichloromethane (25 ml) was heated to reflux for 30 minutes. After cooling down to room temperature 2-phenyl-ethenesulfonic acid amide (for preparation see example 1-1, steps i) and ii)) (500 mg, 2.7 mmol) and DBU (416 mg, 2.7 mmol) were added and the mixture was stirred at room temperature overnight. After washing twice with 1N HCl (50 ml each) and water (50 ml) the mixture was dried over Na2SO4 and concentrated in vacuo. Preparative HPLC (RP18, methanol-water-gradient) returned the title compound (570 mg, 60% yield) as a white solid.

MS: M=350.0 (ESI$^+$) $^1$H-NMR (400 MHz, d$^6$-DMSO): 3.72 (s, 3H); 6.88 (dd, 8.2 Hz, 1.9 Hz, 1H); 6.97 (d, 1.8 Hz, 1H); 7.15 (d, 15.7 Hz, 1H); 7.30 (d, 15,7 Hz, 1H), 7.32–7.44 (m, 4H); 7.51–7.57 (m, 2H)

EXAMPLES 6-2 TO 6-6

The following examples 6-2 to 6-6 were prepared in an analogous manner as described for example 6-1 using the appropriate starting material:

| Example No. | Systematic Name | MS (ESI+, M+H) | $^1$H-NMR |
|---|---|---|---|
| 6-2 | (E)-2-Phenyl-ethenesulfonic acid 2-bromo-4-fluoro-benzoylamide; sodium salt | 382.0 | (400MHz, d$^6$-DMSO)7.13(td, 8.5Hz, 2.6Hz, 1H); 7.19(d, 15.7Hz, 1H); 7.31(d, 15.7Hz, 1H); 7.34–7.44(m, 4H); 7.52–7.57(m, 3H) |
| 6-3 | (E)-2-Phenyl-ethenesulfonic acid 2-bromo-4-methyl-benzoylamide; sodium salt | 378.0 | (400MHz, d$^6$-DMSO)2.27(s, 3H); 7.09(d, 7.8Hz, 1H); 7.18(d, 15.9Hz, 1H); 7.32(d, 15.9Hz, 1H); 7.32–7.43(m, 5H); 7.54(d, 7.3Hz, 2H) |
| 6-4 | (E)-2-Phenyl-ethenesulfonic acid 4-bromo-2-methyl-benzoylamide; sodium salt | 378.1 | (400MHz, d$^6$-DMSO)2.42(s, 3H); 7.15–7.22(m, 1H), 7.26–7.43(m, 6H), 7.51–7.59(m, 3H) |
| 6-5 | (E)-2-Phenyl-ethenesulfonic acid 4-bromo-2-chloro-benzoylamide; sodium salt | 398.0 | (400MHz, d$^6$-DMSO) 7.15–7.22(m, 1H), 7.27–7.48(m, 6H), 7.53–7.60(m, 3H) |
| 6-6 | (E)-2-Phenyl-ethenesulfonic acid 4-chloro-2-methyl-benzoylamide; sodium salt | 334.2 | (400MHz, d$^6$-DMSO)2.43(s, 3H); 7.12–7.23(m, 3H); 7.30–7.44(m, 4H); 7.55(d, 7.6Hz, 2H); 7.62(d, 8.1Hz, 1H) |

Unless stated to the contrary, all compounds in the examples were prepared and characterized as described. All ranges recited herein encompass all combinations and subcombinations included within that range limit. All patents and publications cited herein are hereby incorporated by reference in their entirety for any purpose.

The invention claimed is:

1. Compounds according to formula I and all pharmaceutically acceptable salts or esters thereof wherein formula I is:

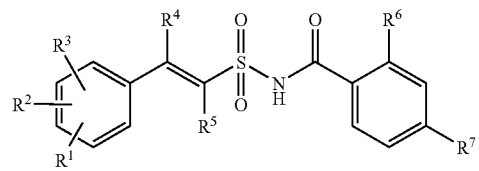

formula I wherein:
(a) $R^1$, $R^2$ and $R^3$ are independently selected from the group consisting of hydrogen, halogen, alkyl, alkoxy, alkylsulfanyl, halogenated alkyl, halogenated alkoxy, halogenated alkylsulfanyl, nitro, amino, alkylamino, dialkylamino, cyano, hydroxyl, and heterocyclyl;
(b) $R^4$ and $R^5$ are independently selected from the group consisting of hydrogen and alkyl;
(c) $R^6$ is selected from the group consisting of chlorine, bromine, methyl, trifluoromethyl, and methoxy; and
(d) $R^7$ is selected from the group consisting of chlorine, bromine, fluorine, methyl, and trifluoromethyl.

2. The compounds according to claim 1, wherein $R^4$ and $R^5$ are both hydrogen.

3. The compounds according to claim 1, wherein $R^6$ and $R^7$ are both chlorine.

4. The compounds according to claim 1, wherein $R^1$, $R^2$ and $R^3$ are independently selected from the group consisting of hydrogen, halogen, alkyl, alkoxy, halogenated alkyl, halogenated alkoxy, dialkylamino, and hydroxy.

5. The compounds according to claim 1, wherein $R^3$ is hydrogen.

6. The compounds according to claim 1, wherein:
(a) $R^1$, $R^2$ and $R^3$ independently represent halogen;
(b) $R^4$ and $R^5$ are both hydrogen; and
(c) $R^6$ and $R^7$ are both chlorine.

7. A compound according to claim 1, selected from the group consisting of:
   (a) (E)-2-(4-Chloro-phenyl)-ethenesulfonic acid 2,4-dichloro-benzoylamide;
   (b) (E)-2-(3-Chloro-phenyl)-ethenesulfonic acid 2,4-dichloro-benzoylamide;
   (c) (E)-2-(2-Chloro-phenyl)-ethenesulfonic acid 2,4-dichloro-benzoylamide;
   (d) (E)-2-(2,4-Difluoro-phenyl)-ethenesulfonic acid 2,4-dichloro-benzoylamide;
   (e) (E)-2-(3,4-Dichloro-phenyl)-ethenesulfonic acid 2,4-dichloro-benzoylamide;
   (f) (E)-2-(2-Fluoro-phenyl)-ethenesulfonic acid 2,4-dichloro-benzoylamide; and
   (g) (E)-2-(2,4,6-Trifluoro-phenyl)-ethenesulfonic acid 2,4-dichloro-benzoylamide; sodium salt.

8. The compounds according to claim 1, wherein:
   (a) $R^1$ and $R^2$ are independently selected from the group consisting of halogenated alkyl and halogenated alkoxy;
   (b) $R^4$ and $R^5$ are both hydrogen;
   (c) $R^3$ is hydrogen; and
   (d) $R^6$ and $R^7$ are both chlorine.

9. The compounds according to claim 1, selected from the group consisting of:
   (a) (E)-2-(4-Trifluoromethyl-phenyl)-ethenesulfonic acid 2,4-dichloro-benzoylamide; and
   (b) (E)-2-(4-Trifluoromethoxy-phenyl)-ethenesulfonic acid 2,4-dichloro-benzoylamide.

10. The compounds according to claim 1, wherein:
   (a) $R^1$ and $R^2$ are independently selected from the group consisting of hydrogen, alkyl, alkoxy, dialkylamino, and hydroxy;
   (b) $R^4$ and $R^5$ are both hydrogen;
   (c) $R^3$ is hydrogen; and
   (d) $R^6$ and $R^7$ are both chlorine.

11. A compound according to claim 1, selected from the group consisting of:
   (a) (E)-2-Phenyl-ethenesulfonic acid 2,4-dichloro-benzoylamide;
   (b) (E)-2-(2,4-Dimethyl-phenyl)-ethenesulfonic acid 2,4-dichloro-benzoylamide;
   (c) (E)-2-(2-Methoxy-phenyl)-ethenesulfonic acid 2,4-dichloro-benzoylamide;
   (d) (E)-2-(2-Dimethylamino-phenyl)-ethenesulfonic acid 2,4-dichloro-benzoylamide;
   (e) (E)-2-o-Tolyl-ethenesulfonic acid 2,4-dichloro-benzoylamide;
   (f) (E)-2-(3-Hydroxy-phenyl)-ethenesulfonic acid 2,4-dichloro-benzoylamide;
   (g) (E)-2-(4-Hydroxy-phenyl)-ethenesulfonic acid 2,4-dichloro-benzoylamide; and
   (h) (E)-2-(2-Hydroxy-phenyl)-ethenesulfonic acid 2,4-dichloro-benzoylamide.

12. The compounds according to any one of claim 1 wherein $R^4$ is alkyl.

13. The compounds according to claim 1, wherein:
   (a) $R^1$ and $R^2$ are independently selected from the group consisting of hydrogen, halogen, alkyl, alkoxy, halogenated alkyl, halogenated alkoxy, and heterocyclyl;
   (b) $R^4$ is alkyl;
   (c) $R^5$ is hydrogen;
   (d) $R^3$ is hydrogen; and
   (e) $R^6$ and $R^7$ are both chlorine.

14. A compound according to claim 1, wherein the compound is:
   (E)-2-Phenyl-propene-1-sulfonic acid 2,4-dichloro-benzoylamide.

15. The compounds according to claim 1 wherein $R^5$ is alkyl.

16. The compounds according to claim 1, wherein:
   (a) $R^1$ and $R^2$ are independently selected from the group consisting of hydrogen, halogen, alkyl, alkoxy, halogenated alkyl, halogenated alkoxy, and heterocyclyl;
   (b) $R^4$ is hydrogen;
   (c) $R^5$ is alkyl;
   (d) $R^3$ is hydrogen; and
   (e) $R^6$ and $R^7$ are both chlorine.

17. A compound according to claim 1 wherein the compound is:
   (E)-1-Phenyl-propene-2-sulfonic acid 2,4-dichloro-benzoylamide.

18. The compounds according to claim 1, wherein $R^6$ is chlorine and $R^7$ is bromine.

19. A compound according to claim 1, selected from the group consisting of:
   (a) (E)-2-(2,4-Dimethyl-phenyl)-ethenesulfonic acid 4-bromo-2-chloro-benzoylamide; sodium salt;
   (b) (E)-2-(3-Methoxy-phenyl)-ethenesulfonic acid 4-bromo-2-chloro-benzoylamide; sodium salt;
   (c) (E)-2-(2-Methoxy-phenyl)-ethenesulfonic acid 4-bromo-2-chloro-benzoylamide; sodium salt;
   (d) (E)-2-(3-Chloro-phenyl)-ethenesulfonic acid 4-bromo-2-chloro-benzoylamide; sodium salt;
   (e) (E)-2-(2-Chloro-phenyl)-ethenesulfonic acid 4-bromo-2-chloro-benzoylamide; sodium salt;
   (f) (E)-2-(3,4-Dichloro-phenyl)-ethenesulfonic acid 4-bromo-2-chloro-benzoylamide; sodium salt;
   (g) (E)-2-Phenyl-ethenesulfonic acid 4-bromo-2-chloro-benzoylamide; sodium salt;
   (h) (E)-2-(4-Trifluoromethyl-phenyl)-ethenesulfonic acid 4-bromo-2-chloro-benzoylamide; sodium salt; and
   (i) (E)-2-(4-Trifluoromethoxy-phenyl)-ethenesulfonic acid 4-bromo-2-chloro-benzoylamide; sodium salt.

20. The compounds according to claim 1, wherein $R^6$ is chlorine and $R^7$ is fluorine.

21. A compound according to claim 1, selected from the group consisting of:
   (a) (E)-2-(3-Methoxy-phenyl)-ethenesulfonic acid 2-chloro-4-fluoro-benzoylamide; sodium salt;
   (b) (E)-2-(2-Methoxy-phenyl)-ethenesulfonic acid 2-chloro-4-fluoro-benzoylamide; sodium salt;
   (c) (E)-2-(3-Chloro-phenyl)-ethenesulfonic acid 2-chloro-4-fluoro-benzoylamide; sodium salt;
   (d) (E)-2-(2,4-Difluoro-phenyl)-ethenesulfonic acid 2-chloro-4-fluoro-benzoylamide; sodium salt;
   (e) (E)-2-(4-Chloro-phenyl)-ethenesulfonic acid 2-chloro-4-fluoro-benzoylamide; sodium salt;
   (f) (E)-2-(4-Methoxy-phenyl)-ethenesulfonic acid 2-chloro-4-fluoro-benzoylamide; sodium salt;
   (g) (E)-2-(4-Trifluoromethyl-phenyl)-ethenesulfonic acid 2-chloro-4-fluoro-benzoylamide; sodium salt;
   (h) (E)-2-(2,4-Dimethyl-phenyl)-ethenesulfonic acid 2-chloro-4-fluoro-benzoylamide; sodium salt;
   (i) (E)-2-(4-Trifluoromethoxy-phenyl)-ethenesulfonic acid 2-chloro-4-fluoro-benzoylamide; sodium salt;
   (j) (E)-2-Phenyl-ethenesulfonic acid 2-chloro-4-fluoro-benzoylamide; sodium salt;
   (k) (E)-2-(3,4-Dichloro-phenyl)-ethenesulfonic acid 2-chloro-4-fluoro-benzoylamide; sodium salt; and (l) (E)-2-(3,5-Dichloro-phenyl)-ethenesulfonic acid 2-chloro-4-fluoro-benzoylamide; sodium salt.

22. The compounds according to claim 1 wherein $R^6$ is bromine and $R^7$ is chlorine.

23. A compound according to claim 1 wherein the compound is:
(E)-2-Phenyl-ethenesulfonic acid 2-bromo-4-chloro-benzoylamide.

24. The compounds according to claim 1 wherein $R^6$ is bromine and $R^7$ is fluorine.

25. A compound according to claim 1, selected from the group consisting of:
(a) (E)-2-(4-Trifluoromethyl-phenyl)-ethenesulfonic acid 2-bromo-4-fluoro-benzoylamide; sodium salt;
(b) (E)-2-(3-Methoxy-phenyl)-ethenesulfonic acid 2-bromo-4-fluoro-benzoylamide; sodium salt;
(c) (E)-2-(2-Methoxy-phenyl)-ethenesulfonic acid 2-bromo-4-fluoro-benzoylamide; sodium salt;
(d) (E)-2-(3-Chloro-phenyl)-ethenesulfonic acid 2-bromo-4-fluoro-benzoylamide; sodium salt;
(e) (E)-2-(2-Chloro-phenyl)-ethenesulfonic acid 2-bromo-4-fluoro-benzoylamide; sodium salt;
(f) (E)-2-Phenyl-ethenesulfonic acid 2-bromo-4-fluoro-benzoylamide; sodium salt;
(g) (E)-2-(4-Trifluoromethoxy-phenyl)-ethenesulfonic acid 2-bromo-4-fluoro-benzoylamide; sodium salt; and
(h) (E)-2-(3,4-Dichloro-phenyl)-ethenesulfonic acid 2-bromo-4-fluoro-benzoylamide; sodium salt.

26. The compounds according to claim 1 wherein $R^6$ is bromine and $R^7$ is methyl.

27. A compound according to claim 1, selected from the group consisting of:
(a) (E)-2-(3-Methoxy-phenyl)-ethenesulfonic acid 2-bromo-4-methyl-benzoylamide; sodium salt;
(b) (E)-2-(2-Methoxy-phenyl)-ethenesulfonic acid 2-bromo-4-methyl-benzoylamide; sodium salt;
(c) (E)-2-(3-Chloro-phenyl)-ethenesulfonic acid 2-bromo-4-methyl-benzoylamide; sodium salt;
(d) (E)-2-(2-Chloro-phenyl)-ethenesulfonic acid 2-bromo-4-methyl-benzoylamide; sodium salt;
(e) (E)-2-Phenyl-ethenesulfonic acid 2-bromo-4-methyl-benzoylamide; sodium salt;
(f) (E)-2-(3,4-Dichloro-phenyl)-ethenesulfonic acid 2-bromo-4-methyl-benzoylamide; sodium salt; and
(g) (E)-2-(4-Trifluoromethoxy-phenyl)-ethenesulfonic acid 2-bromo-4-methyl-benzoylamide; sodium salt.

28. The compounds according to claim 1 wherein $R^6$ is methyl and $R^7$ is chlorine.

29. A compound according to claim 1, selected from the group consisting of:
(a) (E)-2-(3-Chloro-phenyl)-ethenesulfonic acid 4-chloro-2-methyl-benzoylamide; sodium salt;
(b) (E)-2-(2-Chloro-phenyl)-ethenesulfonic acid 4-chloro-2-methyl-benzoylamide; sodium salt;
(c) (E)-2-Phenyl-ethenesulfonic acid 4-chloro-2-methyl-benzoylamide; sodium salt;
(d) (E)-2-(3-Methoxy-phenyl)-ethenesulfonic acid 4-chloro-2-methyl-benzoylamide; sodium salt; and
(e) (E)-2-(2-Methoxy-phenyl)-ethenesulfonic acid 4-chloro-2-methyl-benzoylamide; sodium salt.

30. The compounds according to claim 1 wherein $R^6$ is methyl and $R^7$ is bromine.

31. A compound according to claim 1, selected from the group consisting of:
(a) 2-(3-Methoxy-phenyl)-ethenesulfonic acid 4-bromo-2-methyl-benzoylamide; sodium salt;
(b) (E)-2-(2-Methoxy-phenyl)-ethenesulfonic acid 4-bromo-2-methyl-benzoylamide; sodium salt;
(c) (E)-2-(3-Chloro-phenyl)-ethenesulfonic acid 4-bromo-2-methyl-benzoylamide; sodium salt;
(d) 2-(2-Chloro-phenyl)-ethenesulfonic acid 4-bromo-2-methyl-benzoylamide; sodium salt;
(e) (E)-2-(3,4-Dichloro-phenyl)-ethenesulfonic acid 4-bromo-2-methyl-benzoylamide; sodium salt;
(f) (E)-2-Phenyl-ethenesulfonic acid 4-bromo-2-methyl-benzoylamide; sodium salt;
(g) (E)-2-(4-Trifluoromethyl-phenyl)-ethenesulfonic acid 4-bromo-2-methyl-benzoylamide; sodium salt; and
(h) (E)-2-(4-Trifluoromethoxy-phenyl)-ethenesulfonic acid 4-bromo-2-methyl-benzoylamide; sodium salt.

32. The compounds according to claim 1 wherein $R^6$ is methyl and $R^7$ is fluorine.

33. The compounds according to claim 1 wherein $R^6$ is methyl and $R^7$ is methyl.

34. A compound according to claim 33, selected from the group consisting of:
(a) (E)-2-(3-Methoxy-phenyl)-ethenesulfonic acid 2,4-dimethyl-benzoylamide; sodium salt;
(b) (E)-2-(2-Methoxy-phenyl)-ethenesulfonic acid 2,4-dimethyl-benzoylamide; sodium salt;
(c) (E)-2-(3-Chloro-phenyl)-ethenesulfonic acid 2,4-dimethyl-benzoylamide; sodium salt;
(d) (E)-2-(2-Chloro-phenyl)-ethenesulfonic acid 2,4-dimethyl-benzoylamide; sodium salt;
(e) (E)-2-(3,4-Dichloro-phenyl)-ethenesulfonic acid 2,4-dimethyl-benzoylamide; sodium salt;
(f) (E)-2-(4-Trifluoromethyl-phenyl)-ethenesulfonic acid 2,4-dimethyl-benzoylamide; sodium salt;
(g) (E)-2-(2,4-Dimethyl-phenyl)-ethenesulfonic acid 2,4-dimethyl-benzoylamide; sodium salt; and
(h) (E)-2-(4-Trifluoromethoxy-phenyl)-ethenesulfonic acid 2,4-dimethyl-benzoylamide; sodium salt.

35. The compounds according to claim 1 wherein $R^6$ is trifluoromethyl and $R^7$ is chlorine.

36. A compound according to claim 1 wherein the compound is:
(E)-2-Phenyl-ethenesulfonic acid 4-chloro-2-trifluoromethyl-benzoylamide.

37. The compounds according to claim 1 wherein $R^6$ is trifluoromethyl and $R^7$ is fluorine.

38. A compound according to claim 1, selected from the group consisting of:
(a) (E)-2-(2,4-Dimethyl-phenyl)-ethenesulfonic acid 4-fluoro-2-trifluoromethyl-benzoylamide; sodium salt;
(b) (E)-2-(3-Methoxy-phenyl)-ethenesulfonic acid 4-fluoro-2-trifluoromethyl-benzoylamide; sodium salt;
(c) (E)-2-(3-Chloro-phenyl)-ethenesulfonic acid 4-fluoro-2-trifluoromethyl-benzoylamide; sodium salt;
(d) (E)-2-(2-Chloro-phenyl)-ethenesulfonic acid 4-fluoro-2-trifluoromethyl-benzoylamide; sodium salt;
(e) (E)-2-(4-Trifluoromethoxy-phenyl)-ethenesulfonic acid 4-fluoro-2-trifluoromethyl-benzoylamide; sodium salt;
(f) (E)-2-Phenyl-ethenesulfonic acid 4-fluoro-2-trifluoromethyl-benzoylamide; sodium salt;
(g) (E)-2-(4-Chloro-phenyl)-ethenesulfonic acid 4-fluoro-2-trifluoromethyl-benzoylamide; sodium salt; and
(h) (E)-2-(4-Trifluoromethyl-phenyl)-ethenesulfonic acid 4-fluoro-2-trifluoromethyl-benzoylamide; sodium salt.

39. The compounds according to claim 1 wherein $R^6$ is trifluoromethyl and $R^7$ is methyl.

40. A compound according to claim 1 wherein the compound is:
(E)-2-Phenyl-ethenesulfonic acid 4-methyl-2-trifluoromethyl-benzoylamide.

41. The compounds according to claim 1 wherein $R^6$ is trifluoromethyl and $R^7$ is trifluoromethyl.

42. A compound according to claim 1, selected from the group consisting of:
(a) (E)-2-(2,4-Dimethyl-phenyl)-ethenesulfonic acid 2,4-bis-trifluoromethyl-benzoylamide; sodium salt;
(b) (E)-2-(3-Methoxy-phenyl)-ethenesulfonic acid 2,4-bis-trifluoromethyl-benzoylamide; sodium salt;
(c) (E)-2-(2-Methoxy-phenyl)-ethenesulfonic acid 2,4-bis-trifluoromethyl-benzoylamide; sodium salt;
(d) (E)-2-(3-Chloro-phenyl)-ethenesulfonic acid 2,4-bis-trifluoromethyl-benzoylamide; sodium salt;
(e) (E)-2-(2-Chloro-phenyl)-ethenesulfonic acid 2,4-bis-trifluoromethyl-benzoylamide; sodium salt;
(f) (E)-2-Phenyl-ethenesulfonic acid 2,4-bis-trifluoromethyl-benzoylamide; sodium salt;
(g) (E)-2-(2,4-Difluoro-phenyl)-ethenesulfonic acid 2,4-bis-trifluoromethyl-benzoylamide; sodium salt; and
(h) (E)-2-(4-Chloro-phenyl)-ethenesulfonic acid 2,4-bis-trifluoromethyl-benzoylamide; sodium salt.

43. The compounds according to claim 1, wherein $R^6$ is methoxy and $R^7$ is chlorine.

44. A compound according to claim 1, selected from the group consisting of:
(a) (E)-2-(3-Methoxy-phenyl)-ethenesulfonic acid 4-chloro-2-methoxy-benzoylamide; sodium salt;
(b) (E)-2-Phenyl-ethenesulfonic acid 4-chloro-2-methoxy-benzoylamide; sodium salt; and
(c) (E)-2-(3-Chloro-phenyl)-ethenesulfonic acid 4-chloro-2-methoxy-benzoylamide; sodium salt.

45. The compounds according to claim 1 wherein $R^6$ is methoxy and $R^7$ is bromine.

46. A compound according to claim 1, wherein the compound is:
(E)-2-Phenyl-ethenesulfonic acid 4-bromo-2-methoxy-benzoylamide.

47. A compound according to claim 1 wherein $R^6$ is methoxy and $R^7$ is fluorine.

48. A compound according to claim 1 wherein the compound is:
(E)-2-Phenyl-ethenesulfonic acid 4-fluoro-2-methoxy-benzoylamide.

49. The compounds according to claim 1, wherein $R^6$ is methoxy and $R^7$ is trifluoromethyl.

50. A compound according to claim 1 wherein the compound is:
(E)-2-Phenyl-ethenesulfonic acid 2-methoxy-4-trifluoromethyl-benzoylamide.

51. A process for the preparation of the compounds of formula I according to claim 1, comprising the steps of:
a) reacting a compound of formula II:

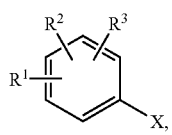

formula II wherein $R^1$, $R^2$ and $R^3$ are defined according to formula I in claim 1 and X is iodine or bromine, with ethenesulfonic acid (1,1,3,3-tetramethyl-butyl)-amide:

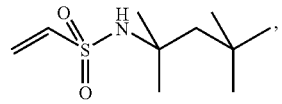

to obtain the compounds of formula IIIa:

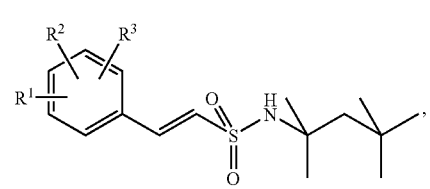

formula IIIa wherein $R^1$, $R^2$ and $R^3$ are defined according to formula I in claim 1, b) cleaving the 1,1,3,3-tetramethyl-butyl group of the compounds of formula IIIa to obtain the free sulfonamides of formula IVa:

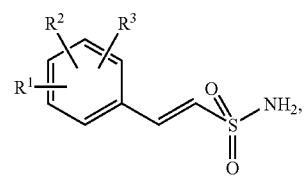

formula IVa wherein $R^1$, $R^2$ and $R^3$ have the significance given for formula I in claim 1, and c) reacting the sulfonamides of formula IVa with the benzoic acid of formula XI:

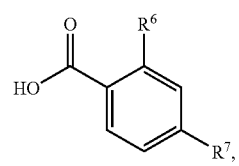

formula XI which is activated before, and wherein $R^6$ and $R^7$ are defined according to formula I in claim 1;

to obtain the compounds of formula Ia:

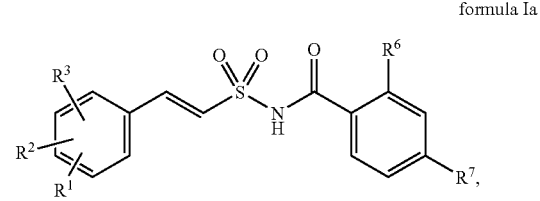

formula Ia wherein $R^1$, $R^2$, $R^3$, $R^6$ and $R^7$ are defined according to formula I in claim 1.

52. A process for the preparation of the compounds of formula I according to claim 1, comprising the steps of:
a) reacting a compound of formula V:

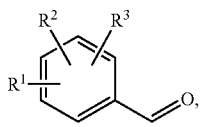

formula V wherein $R^1$, $R^2$ and $R^3$ are defined according to claim 1,
with N-(1,1,3,3-tetramethyl-butyl)-methanesulfonamide:

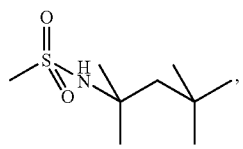

to obtain the compounds of formula VI:

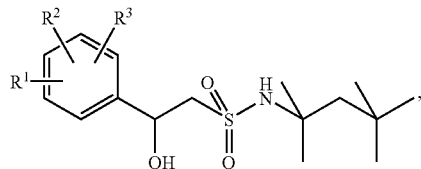

formula VI wherein $R^1$, $R^2$ and $R^3$ are defined according to formula I in claim 1,
b) dehydrating the compounds of formula VI to obtain the compounds of formula IIIa:

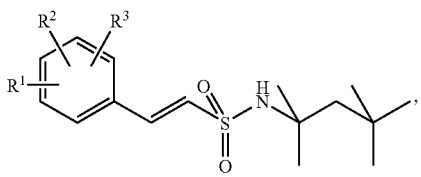

formula IIIa wherein $R^1$, $R^2$ and $R^3$ are defined according to formula I in claim 1,
c) cleaving the 1,1,3,3-tetramethyl-butyl group of the compounds of formula IIIa to obtain the free sulfonamides of formula IVa:

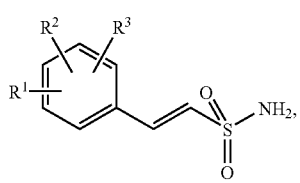

formula IVa wherein $R^1$, $R^2$ and $R^3$ are defined according to formula I in claim 1, and
d) reacting the sulfonamides of formula IVa with the benzoic acid of formula XI:

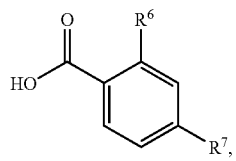

formula XI which is activated before and wherein $R^6$ and $R^7$ are defined according to formula I in claim 1;
to obtain the compounds of formula Ia:

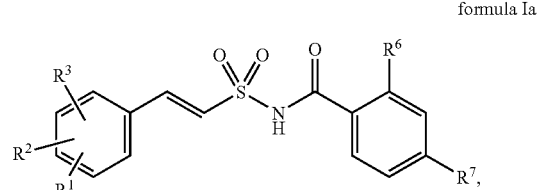

formula Ia wherein $R^1$, $R^2$, $R^3$, $R^6$ and $R^7$ are defined according to formula I in claim 1.

53. A process for the preparation of the compounds of formula I according to claim 1 comprising:
reacting a compound of formula IV:

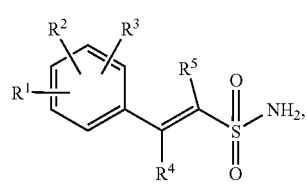

formula IV wherein $R^1$, $R^2$, $R^3$, $R^4$ and $R^5$ are defined according to formula I in claim 1,
with the benzoic acid of formula XI:

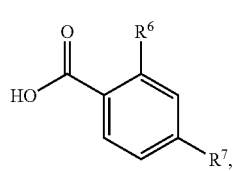

formula XI which is activated before and wherein $R^6$ and $R^7$ are defined according to formula I in claim 1;

to obtain the compounds of formula I:

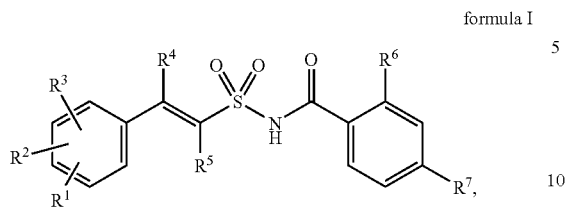

formula I wherein $R^1$, $R^2$, $R^3$, $R^4$, $R^5$, $R^6$ and $R^7$ are defined according to formula I in claim 1.

54. A process for the preparation of the compounds of formula I according to claim 1 comprising:

reacting a compound of formula VIII:

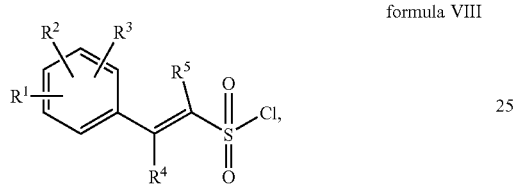

formula VIII wherein $R^1$, $R^2$, $R^3$, $R^4$ and $R^5$ are defined according to formula I in claim 1, with the benzamide of formula X:

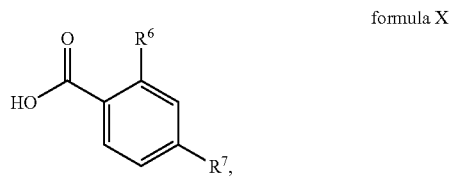

formula X wherein $R^6$ and $R^7$ are defined according to formula I in claim 1;
to obtain the compounds of formula I:

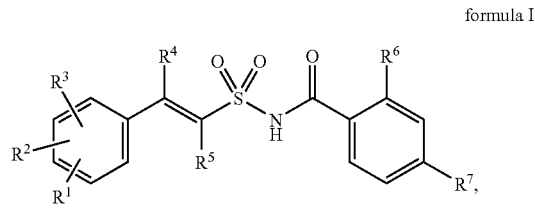

formula I wherein $R^1$, $R^2$, $R^3$, $R^4$, $R^5$, $R^6$ and $R^7$ are defined according to formula I in claim 1.

55. A pharmaceutical composition comprising a therapeutically effective amount of a compound of claim 1 and a pharmaceutically acceptable carrier.

* * * * *